United States Patent [19]

Pfaendler et al.

[11] Patent Number: 5,096,899
[45] Date of Patent: Mar. 17, 1992

[54] OXAPENEM-3-CARBOXYLIC ACIDS

[75] Inventors: Hans R. Pfaendler, Munich; Wolfram Hendel, Cologne, both of Fed. Rep. of Germany

[73] Assignee: Bayer Aktiengesellschaft, Leverkusen, Fed. Rep. of Germany

[21] Appl. No.: 574,573

[22] Filed: Aug. 24, 1990

Related U.S. Application Data

[63] Continuation of Ser. No. 382,596, Jul. 19, 1989, abandoned, which is a continuation of Ser. No. 226,255, Jul. 29, 1988, abandoned.

[30] Foreign Application Priority Data

Jul. 31, 1987 [DE] Fed. Rep. of Germany ........ 3725375

[51] Int. Cl.$^5$ ................. A61K 31/42; C07D 498/047; C07D 205/09; C07D 205/10
[52] U.S. Cl. .................................... 514/210; 540/347; 540/360; 540/361
[58] Field of Search ..................... 514/210; 540/347

[56] References Cited

FOREIGN PATENT DOCUMENTS 0018305 10/1980 European Pat. Off. .
2747350 4/1978 Fed. Rep. of Germany .
2808116 9/1978 Fed. Rep. of Germany .
1591438 12/1978 United Kingdom .

OTHER PUBLICATIONS

Bentley JCS Chem. Comm.
Cherry, JCS Chem. Comm. 1978, 469–470.
Bentley J.C.S. Chem. Comm. 1977, 905.
Cherry, J.C.S. Chem. Comm. 1978, 469–470.
Current Antibicrobial Patents 1989, pp. 1067–1068.

*Primary Examiner*—Mark L. Berch
*Attorney, Agent, or Firm*—Sprung Horn Kramer & Woods

[57] ABSTRACT

Compounds of the structural formulae

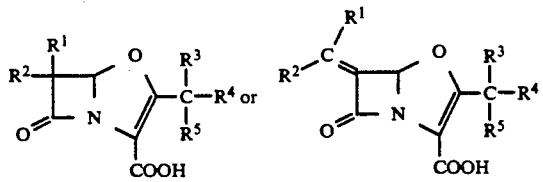

and their pharmaceutically acceptable salts, esters and amide derivatives, in which $R^1$ and $R^2$, independently of one another, denote hydrogen or pharmaceutically acceptable groups which have 1 to 10 carbon atoms and are bonded to the remaining part of the molecule via carbon-carbon single bonds, and in which $R^3$, $R^4$ and $R^5$, independently of one another, denote pharmaceutically acceptable groups which have 1 to 10 carbon atoms and are bonded to the remaining part of the molecule via carbon-carbon single bonds, are useful antibiotics.

The trisubstitution by three groups $R^3$, $R^4$ and $R^5$, which are bonded via carbon-carbon single bonds, results in a noticeable increase in the hydrolysis stability and thus also in the antibacterial action of axapenemcarboxylic acids.

12 Claims, No Drawings

OXAPENEM-3-CARBOXYLIC ACIDS

This application is a continuation, of application Ser. No. 382,596, filed July 19, 1989, now abandoned. Which is a continuation of application Ser. No. 226,255, filed July 29, 1988 now abandoned.

The invention relates to 1-oxopenem-3-carboxylic acids of the following structures.

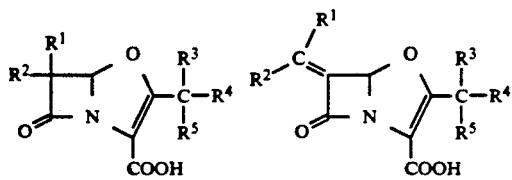

in which $R^1$ and $R^2$, independently of one another, denote hydrogen or pharmaceutically acceptable groups which are bonded via carbon atoms, and $R^3$, $R^4$ and $R^5$, independently of one another, denote pharmaceutically acceptable groups which are bonded to the exocyclic, allylic carbon atom via carbon atoms. These compounds and their pharmaceutically acceptable salts, esters and amide derivatives are useful antibiotics. The invention furthermore relates to processes for the preparation of such compounds, pharmaceutical preparations containing these compounds, and methods of treatment in which these compounds and preparations are administered if an antibiotic action is indicated.

The invention relates to 6-unsubstituted, 6-monosubstituted or 6,6-disubstituted 1-oxapen-2-em-3-carboxylic acids which are provided with particular radicals in the 2-position. These radicals are characterized in that they contain a central carbon atom which is bonded directly to the oxapenem nucleus and to which are bonded three further groups bonded via C atoms. These compounds are useful antibiotics and may be represented by the general structural formulae

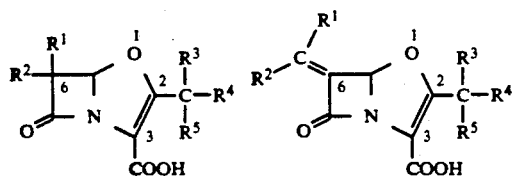

in which $R^1$ and $R^2$, independently of one another, are selected from: hydrogen or the pharmaceutically acceptable groups which are bonded to the remaining part of the molecule by C—C single bonds and which contain: substituted or unsubstituted alkyl, alkenyl, alkinyl, cycloalkyl, alkylcycloalkyl, alkylcylcoalkenyl, cycloalkylalkyl, alkenylcycloalkyl, cycloalkenylalkyl, aryl, aralkyl, aralkenyl, aralkinyl, carboxyl or cyano, where the foregoing alkyl, alkenyl or alkinyl molecule parts contain 1 to 6 carbon atoms, and the cycloalkyl or cycloalkenyl molecule parts contain 3 to 6 carbon atoms and the aryl molecule parts contain 6 to 10 carbon atoms, heteroaryl, heteroaralkyl, heteroaralkenyl, heteroaralkinyl, alkylheteroaryl, heterocyclyl, heterocyclylalkyl, heterocyclylalkenyl, heterocyclalkinyl or alkylheterocyclyl, where the foregoing alkyl, alkenyl or alkinyl molecule parts contain 1 to 6 carbon atoms and the heteroaromatic or heterocyclic molecule part is monocyclic or bicyclic and contains 3 to 10 ring atoms, of which one or more are selected from the series comprising: oxygen, sulphur and nitrogen, and where the substituents of the abovementioned groups may be: protected or unprotected hydroxyl, hydroxyalkoxy, aminoalkoxy, amidinoalkoxy, alkoxy, acyloxy, aryloxy, heteroaryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheteroarylthio, hydroxyalkylheteroarylthio, heterocyclylthio, carbamoylthio, alkylcarbamoylthio, thiocarbamoylthio or alkylthiocarbamoylthio, protected or unprotected amino or monoalkylamino, dialkylamino, oxo, protected or unprotected oximino or alkylamino, tetraalkylammonium, cycloalkylamino, arylamino, heteroarylamino, heterocyclylamino, acylamino, amidino, alkylamidino, guanidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents, independently of one another, occur once or several times and their alkyl molecule part contains 1 to 6 carbon atoms and their aryl molecule part contains 6 to 10 carbon atoms, and where the heteroaromatic or heterocyclic molecule part is monocyclic or bicyclic and contains 3 to 10 ring atoms, of which one or more are selected from the series comprising: oxygen, sulphur and nitrogen, and characterized in that $R^3$, $R^4$ and $R^5$, independently of one another, are selected from the abovementioned, pharmaceutically acceptable groups which are bonded to the remaining part of the molecule via carbon-carbon single bonds.

The groups $R^3$, $R^4$ and $R^5$ are selected independently from the pharmaceutically acceptable groups as described above, which are bonded to the remaining part of the molecule by C—C single bonds.

The protecting groups for the abovementioned, protected substituents are easily removable radicals which are known per se, as are usually used for this purpose in organic synthesis. Protecting groups of this type are found, for example, in T. W. Greene, "Protective Groups in Organic Synthesis", Wiley, N.Y., 1981.

In addition, it is possible for two of the groups $R^3$, $R^4$ and $R^5$ to be bridged by molecule parts containing carbon, oxygen, nitrogen and sulphur; in this case, they are a component of a carbocyclic or heterocyclic ring, which may have three, four, five or six members.

In addition, it is possible for the two groups $R^1$ and $R^2$ to be bridged by molecule parts containing carbon, oxygen, nitrogen and sulphur; in this case, they are a component of a three-, four-, five- or six-membered carbocyclic or heterocyclic ring.

Examples of bridging molecule parts for $R^1$ and $R^2$ or for $R^3$ and $R^4$ are methylene, dimethylene, trimethylene tetramethylene, oxamethylene, oxadimethylene, dioxamethylene, azadimethylene, diazamethylene or the like.

Pharmaceutically acceptable groups $R^1$, $R^2$, $R^3$, $R^4$ and $R^5$, which are bonded via C—C single bonds, are groups as are customary, for example, in β-lactam antibiotics. Such groups are found, for example, in M. S. Sassiver, A. Lewis in "Advances in Applied Microbiology", Ed. D. Perlman, Academic Press, N.Y. (1970).

The invention furthermore relates to the pharmaceutically acceptable salts, esters and amide derivatives of the compounds (I) and (II) according to the invention.

The invention furthermore relates to processes for the preparation of such compounds (I) and (II), pharmaceutical preparations containing such compounds and methods of treatment in which these compounds and preparations are administered if an antibiotic action is indicated.

There is a constant demand for new antibiotics. Unfortunately, there is no static activity in the case of any given antibiotic since, on continuous use on a large scale, selectively resistant strains of pathogenic bacteria are newly formed. Accordingly, the search for new antibiotics continues.

In addition to classic β-lactam antibiotics, i.e. penicillins and cephalosporins, so-called nonclassical or nontraditional β-lactam antibiotics are also employed today against diseases caused by bacterial infection. The most important compounds of this type used today are the penems and the carbapenems. A recent book deals with the synthesis and pharmacology of these active compounds: Chemistry and Biology of β-lactam Antibiotics Vol. 2 (Nontraditional β-lactam antibiotics), ed. by R. B. Morin and M. Gorman, Academic Press, N.Y. (1982).

Due to the close structural relationship between the oxapenemcarboxylic acids and the sulphur-containing penemcarboxylic acids or the carbapenemcarboxylic acids, it could have been presumed that oxapenem-3-carboxylic acids would also have an antibacterial action (Tetrahedron 38 (16) 2489-2504 (1982), page 2489).

Although an antibacterial activity has been mentioned for oxapenem-3-carboxylic acids, for example in U.S. Pat. No. 4,173,895 or EP 80,710,008.6, it has never been supported by experimental data. The only available measurement data on their antibacterial activity are to be found in "Chemistry and Biology of β-Lactam Antibiotics, Vol. 2 Nontraditional β-Lactam Antibiotics" ed. by R. B. Morin and M. Gorman, page 383:

"(The potassium salt of 2-ethyl-1-oxapenem-3-carboxylic acid) was too unstable for testing of the antibacterial activity or the synergism with ampicillin against intact bacteria".

A compound, 2-ethyl-1-oxapen-2-em-3-carboxylic acid, which has been presented as active in earlier patent applications was thus in actual fact much too unstable in aqueous media for antibacterial testing and thus ineffective in practice as an antibiotic. Only inhibition of isolated bacterial enzymes (β-lactamases) could be detected.

The instability of oxapenem-3-carboxylic acids, also called clavemcarboxylic acids, which have been disclosed earlier, is apparent in the preparation of methyl esters, for example in J.C.S. Chem. Commun. 1977, 720. These too were unstable.

The low importance of the oxapenem-3-carboxylic acids which have virtually no antibacterial activity or an only low activity may also be gathered from the fact that, in a 402 page book on nonclassical β-lactam antibiotics (Chemistry and Biology of β-Lactam Antibiotics, Vol. 2, ed. by R. B. Morin and M. Gorman, Academic Press, New York (1982), only 5 pages (pages 381-385) are dedicated to them.

There was much less interest still in oxapenem-3-carboxylic acids in the subsequent years (1982-1986), which is confirmed by a full literature search in Chemical Abstracts. Under the systematic name 4-oxa-1-azabicyclo[3.2.0]hept-2-ene-2-carboxylic acid, it was found that research in this area decreased constantly: 1977: 3, 1978: 9, 1979: 2, 1980: 6, 1981: 9, 1982: 2, 1983: 5, 1984: 2, 1985: 0 and 1986: 0 publications. Due to their low stability and due to their low antibacterial activity, the oxapenem-3-carboxylic acids had thus become unimportant to experts in the field. Compared with the interest in other nonclassical β-lactam antibiotics, the low interest in oxapenem-3-carboxylic acids shows that experts in the field are at present prejudiced agains the practicability and activity of the oxapenem-3-carboxylic acids class of compounds.

The stability of β-lactam antibiotics has always been a central problem in this class of active compounds. Thus, for example, hundreds of thousands of soldiers died in the Second World War from wound infections since, due to the instability of penicillin, it was impossible to produce sufficient material to cure the patients. In was only later, with the discovery of the more stable, crystalline penicillins (penicillin V and penicillin G), that production from mould fungi succeeded on a thousand tonne scale.

The stability also plays an important role in nonclassical β-lactam antibiotics: thienamycin, currently the most active natural antibiotic "in vitro", is very sensitive to hydrolysis and can therefore not be employed as a therapeutic agent. It was only later that a suitable more stable derivative (formiminothienamycin=MK-0787) was prepared (Lit.: Recent Advances in the Chemistry of β-Lactam Antibiotics, ed. by G. I. Gregory, The Royal Society, London, page 249 (1981)).

The customary oxapenem-3-carboxylic acids are very unstable substances. There was therefore a demand, even in this class of substances, for the preparation of stable derivatives which have a greatly improved antibacterial action and which survive long enough in aqueous medium to reach the site of action intact in order to kill pathogenic bacteria.

It has now been found that oxapenem-3-carboxylic acids of the formulae I and II are much more stable than the compounds disclosed earlier. Exact measurements under physiological conditions, i.e. in aqueous phosphate buffer at pH 7.4° and 37° C., with the aid of UV spectroscopy showed a surprising dependency of the stability of the compounds III on the substituents $R^1$, $R^2$, $R^3$, $R^4$ and $R^5$.

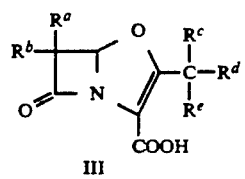

III

| Compound (III) | Half value period for hydrolysis pH 7.4, 37° C. (measure of stability) |
|---|---|
| (a) $R^a$, $R^b$, $R^c$, $R^d$ and $R^e$ = CH$_3$ | 30 hours |
| (b) $R^a$, $R^b$, $R^c$ and $R^d$ = CH$_3$; $R^e$ = H | 2 hours |
| (c) $R^a$, $R^b$ and $R^c$ = CH$_3$; $R^d$ and $R^e$ = H | 70 minutes |
| (d) $R^a$ and $R^b$ = CH$_3$; $R^c$, $R^d$ and $R^e$ = H | 50 minutes |

-continued

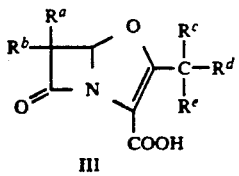

III

| Compound (III) | Half value period for hydrolysis pH 7.4, 37° C. (measure of stability) |
|---|---|
| (e) $R^a$, $R^b$, $R^c$, $R^d$ and $R^e$ =H | a few minutes |

Compound IIIa is identical to I ($R^1$, $R^2$, $R^3$, $R^4$ and $R^5$=CH$_3$).

By means of these measurements, it was proven for the first time that groups $R^c$, $R^d$ and $R^e$, which are bonded by carbon, cause significant stabilization of the oxapenem-3-carboxylic acid. Even a single group $R^c$, $R^d$ or $R^e$=H results in a drastic reduction in stability!

The compound IIIe, described as preferred in earlier patent applications (for example in EP 18,305), hydrolyses in a few minutes and could never efficiently be transported through the bloodstream to the site of action undamaged. Due to immediate hydrolysis, however, IIIe has virtually no antibacterial activity, even in vitro. When using Staphylococcus aureus DSM 1104, an inhibiting zone of only a few mm was observed in the agar diffusion test after applying 250 μg of IIIe.

It has furthermore been found that the compounds of the formulae I and II have a high activity against Staphylococcus aureus. Certain representatives are also active against Gram-positive and Gram-negative germs and resistant bacteria. Thus, the compound (I) ($R^1$ and $R^2$=H; $R^3$, $R^4$ and $R^5$=CH$_3$), which is distinguished from IIIe, which has virtually no antibacterial activity, only by containing three additional methyl groups, produces the following inhibiting zone diameters in the agar diffusion test after application of 200 μg of substance:

| Staph. aureus DSM 1104 | 45 mm |
|---|---|
| Staph. aureau 012484/77 (penicillin- and cephalosporin-resistant) | 47 mm |
| Escherichia coli DSM 1103 | 41 mm |

By suitable substitution it was possible to considerably increase the activity against certain germs. Thus, for example, the compound (I) ($R^1$=H; $R^2$=CH$_2$OH; $R^3$, $R^4$ and $R^5$=CH$_3$) exhibits the following inhibiting zone diameters after application of only 10 μg of substance:

| Staph. aureus DSM 1104 | 30 mm |
|---|---|
| Staph. aureau 012484/77 | 32 mm |
| Escherichia coli DSM 1103 | 30 mm |
| Escherichia coli W 3110 R6K (TEM 1) (forming β-lactamase) | 29 mm |

The above data show that, due to the compounds according to the invention, the oxapenem-3-carboxylic acid class, which was hitherto regarded as having virtually no antibacterial activity and consequently as unimportant, appears for the very first time amongst the most active antibacterial agents. Penicillin V (130 μg) exhibited a strong inhibitory action only against Staph. aureus 1104 (42 mm) and a minimal action against E. coli DSM 1103 (13 mm). The two other germs were not inhibited. Comparable data on the antibacterial activity of the natural antibiotic thienamycin can be found in Journ. Amer. Chem. Soc. 100, 8004 (1978): the inhibiting zone diameters after application of 25 μg of substance was 2841 mm here when similar germs were used.

The present invention therefore has the object of providing a new class of antibiotics which is important in verterinary and human therapy and in inanimate systems. These antibiotics are active against many Gram-positive, Gram-negative, penicillin-resistant and cephalosporin-resistant bacteria. The prerequisite for this high activity and applicability is provided by the trisubstitution of the exocyclic, allylic carbon atom of I and II by three groups $R^3$, $R^4$ and $R^5$ bonded via carbon atoms. The superior antibacterial activity of the oxapenem-3-carboxylic acids according to the invention could not be expected to this extent from the prior art. In addition, chemical processes for preparation of these antibiotics and their non-toxic pharmaceutically acceptable salts; pharmaceutical preparations containing these antibiotics; and methods of treatment in which these antibiotics and the preparations are administered if an antibiotic action is indicated are to be provided according to the invention.

The compounds of the above formulae I and II according to the invention are expediently prepared in accordance with the following equation:

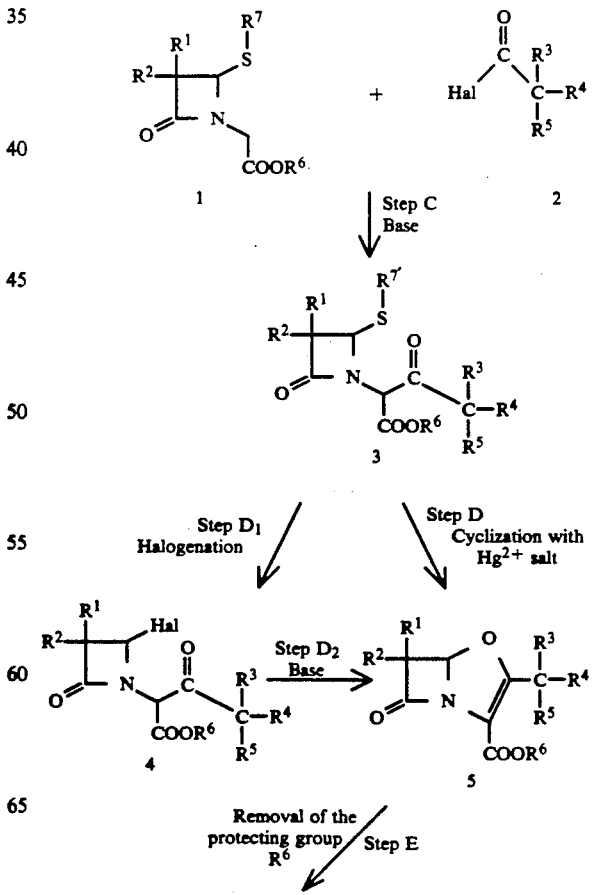

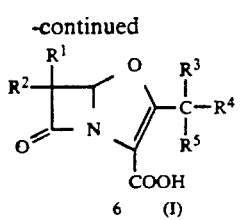

Compounds II are expediently obtained according to the following reaction equation:

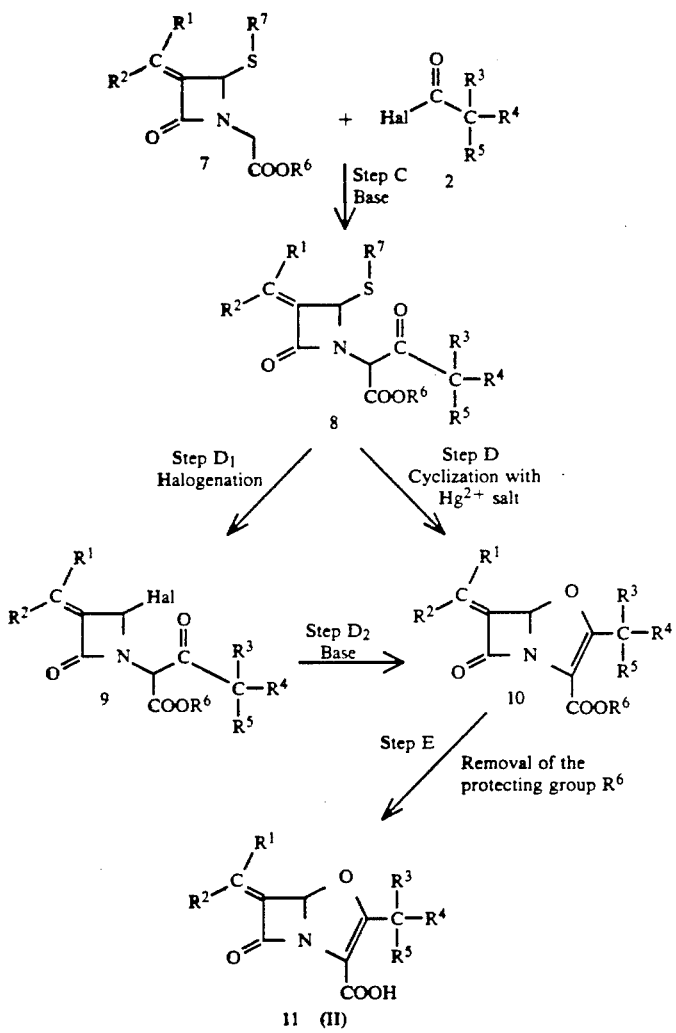

In which, in both reaction equations, $R^1$, $R^2$, $R^3$, $R^4$ and $R^5$ have the abovementioned definitions, $R^6$ denotes an easily removable protecting or masking group, and $R^6$ may likewise be the molecule part of a pharmaceutically acceptable ester. The protecting group $R^6$ is typically an acyl group, such as lower alkanoyl, aralkylcarbonyl or the like, such as acetyl, bromo-tert-butoxycarbonyl, benzyloxycarbonyl, formyl, trifluoroacetyl and the like, or a trialkylsilyl group, such as trimethylsilyl or tert-butyldimethylsilyl; and the protecting group $R^6$ is typically a substituted or unsubstituted alkyl, aralkyl, alkenyl or similar group, such as benzyl, o-nitrobenzyl, p-nitrobenzyl, trimethoxybenzyl, 2-oxopropyl, 2-oxo-2-phenylethyl, allyl, 2-cyanoethyl, 2-trimethylsilyloxyethyl, 2,2,2-trichloroethyl, pivaloyloxymethyl, bromo-tert-butyl and the like.

$R^7$ is typically a substituted or unsubstituted, branched or unbranched alkyl group, aralkyl group, aryl group, heteroaryl or heteroaralkyl group, where the substituents denote lower alkyl, acyloxy, chlorine, bromine, nitro, lower alkoxy, cyano and the like, and the heteroatoms of the heteroaryl or heteroaralkyl part are selected from the series comprising oxygen, nitrogen and sulphur. Particularly typical radicals $R^7$ are methyl, ethyl, propyl, isopropyl, butyl, phenyl, tolyl, benzyl, triphenylmethyl, tert-butyl, 2-mercaptobenzothiazolyl and the like.

The above reaction diagrams are described in greater detail below in words. A suitably substituted azetidinone (1) or (7) is reacted with the acyl halide (2) in the presence of about 1 or 2 equivalents of a base such as butyllithium, lithium diisopropylamide or lithium bis-(trimethylsilylamide) and the like at a low temperature of about $-70°$ C. to $0°$ C. over the course of about one hour to form 3 or 8 respectively. The identity of the solvent is not crucial, provided only that the reaction participants are soluble and that it is inert or essentially inert during the reaction. In the reaction (1→3) or (7→8), tetrahydrofuran, dioxane, glyme, dimethylformamide or a mixture of these solvents with hexane is expediently used.

The reaction (3→4) or (8→9) may be carried out by any known halogenation process. Suitable halogenating agents are chlorine, bromine, iodine, sulphuryl chloride and the like. In a preferred halogenation process, 3 or 8 is treated with 1 or 2 equivalents of chlorine in an inert solvent, such as, for example, carbon tetrachloride, toluene or methylene chloride. This reaction is typically carried out for 0.5 to 2 hours at a temperature between about −70° C. and 0° C.

In the reaction (4→5) or (9→10), 4 or 9 is reacted with about 1 or 2 equivalents of a base, such as, for example, sodium methoxide, potassium tert-butoxide, sodium phenoxide, sodium thiophenoxide, diazabicycloundecene and the like, in a suitable inert solvent, such as, for example, toluene, tetrahydrofuran or dimethylformamide, to give 5 or 10 respectively. The typical reaction time is about 30 minutes to 2 hours, and the typical reaction temperature about −70° C. to room temperature.

In the direct cyclization reaction (3→5) or (8→10), 3 or 8 is reacted with 1-3 equivalents of a mercury(II) salt, such as, for example, mercury chloride, in a suitable inert solvent, such as, for example, glyme, dioxane or tetrahydrofuran, to give 5 or 10 respectively. Mixtures of two or more mercury(II) salts, for example a 1:1 mixture of mercury(II) oxide and mercury(II) chloride, are also typically used. The typical reaction temperature is 60°-100° C. and the typical reaction time 2 to 20 hours.

The protecting group is removed (5→6) or (10→11) by processes which are well known per se, such as catalytic hydrogenation, hydrolysis, reduction, nucleophilic substitution, solvolysis and the like. Suitable hydrogenation catalysts for removing the protecting group are platinum metals and their oxides, Raney nickel, palladium on charcoal and the like; suitable solvents for the hydrogenation are methanol, ethanol, ethyl acetate/$H_2O$, ethanol/$H_2O$ and the like, in the presence of hydrogen at a pressure of 1 to 50 atm. The hydrogenation typically takes 5 minutes to 2 hours at a temperature of 0°-25° C. and is optionally carried out in the presence of a weak base, for example sodium hydrogen carbonate. In the case of hydrolytic degradation of the protecting group, 1 equivalent of a base, such as, for example, dilute aqueous sodium hydroxide solution or the like, is added to 5 or 10 in a suitable solvent, such as, for example, tetrahydrofuran or tetrahydrofuran/$H_2O$. The reaction typically takes 5-60 minutes; the reaction temperature is −30° to 0° C. In the case of reductive degradation of the protecting group, 1-3 equivalents of a reducing agent, for example zinc dust or the like, is added to 5 or 10 in a suitable solvent, for example acetic acid/water. The reaction typically takes 30 minutes to 2 hours; the reaction temperature is −30° C. to room temperature. In the case of degradation of the protecting group by nucleophilic substitution, 5 or 10 is reacted with a nucleophilic agent, for example tetrabutylammonium fluoride or the like, in an inert solvent, for example tetrahydrofuran. The reaction typically takes 30 minutes to 2 hours; the reaction temperature is −30° C. to room temperature. In the case of degradation of the protecting group by solvolysis, 1 or 2 equivalents of a Lewis acid, for example aluminium trichloride, and subsequently a solvolysing solvent, for example water, are added to 5 or 10 in a suitable solvent, for example tetrahydrofuran. The reaction typically takes 30 minutes to 2 hours; the reaction temperature is 0° C. to room temperature.

Some of the trisubstituted acetyl chlorides (2) are commercially available, such as, for example, pivaloyl chloride or 3-chloropivaloyl chloride, or are known from the literature, such as, for example, 2-methyl-2-phenylpropanoyl chloride (Helv. Chim. Acta 54, 870 (1971); J. Org. Chem. 39, 3268 (1974)) or 3-acetoxypivaloyl chloride (Bull. Chem. Soc. France 31, 125 (1904); J. Org. Chem. 24, 1228 (1959)) or can be prepared analogously to similar known substances, such as, for example, 2-methyl-2-thienylpropanoyl chloride by the synthetic procedure for the phenyl derivative.

Surprisingly, it has been found that, due to the trisubstitution of the α-carbon atom by the groups $R^3$, $R^4$ and $R^5$ bonded via carbon atoms, the compounds of the formulae 3 or 8 and 4 or 9 exist exclusively as ketones, which can be seen by the absence of NMR enol resonances at 11.6 ppm (Tetrahedron 38, (16), 2489-2504 (1982), page 2490) and the presence of a ketone carbonyl band at −1720 cm$^{-1}$ and a saturated carboxylate band at −1755 cm$^{-1}$ in the IR spectrum recorded in methylene chloride. The ketone structure is also shown by the lack of reactivity: thus, these compounds, applied in methylene chloride onto a filter paper and sprayed with aqueous iron(III) chloride solution, do not produce a violet coloration. Neither are the ketones of the formulae 3 or 8 and 4 or 9 converted into the enol ethers when treated with diazomethane solution in ether. All these findings, conflict with previously disclosed intermediates without the trisubstitution according to the invention; these existed exclusively or principally as enols (for example in EP 0,018,305 A1, page 3; Tetrahedron 38, (16), 2490 (1982); J.C.S. Chem. Comm. 1977, 720 and J.C.S. Chem. Comm. 1977, 905).

This shows that compounds of the formulae 3 or 8 and 4 or 9 have never been prepared before and have never been further reacted before. Since the final products I and II can only be prepared via ketonic intermediates, it also demonstrates the novelty of I and II. Although oxapenem-3-carboxylic acids containing branched aliphatic radicals in the 2-position were mentioned in earlier patent applications (for example in EP 0,018,305 A1), these cannot be compounds I or II according to the invention since they were prepared from enols.

When chiral azetidin-2-ones of the formulae 1 or 7 having the 4R configuration are used, chiral 1-oxapen-2-em-3-carboxylic acids (I) and (II) respectively which likewise have the 5R configuration are obtained, if appropriate in accordance with the reaction equations (1→6) or (7→11) described.

A variant of the synthesis of compounds (I) and (II) may arise by modifying the groups $R^3$, $R^4$ and/or $R^5$ at the ketone stage 3 or 8. Thus, for example a group $R^3$=alkyl-Cl can be converted into a group $R^3$=alkyl-$N_3$ using nucleophiles, such as, for example, tetraalkylammonium azide. A typical solvent for the illustrative reaction is DMF. The typical reaction temperature is 0° C. to 80° C. and the reaction typically takes 2-48 hours.

An advantageous variant of the synthesis of compounds (I) and (II) may arise by removing several protecting groups in the (5→6) or (10→11) step. Thus, for example, protected hydroxyalkyl groups $R^1$ and $R^2$, but also protected hydroxyalkyl or protected aminoalkyl groups $R^3$, $R^4$ and/or $R^5$, can also be liberated simultaneously on removal of the protecting group $R^6$.

The synthesis of the starting material 1 is described below. 1 is prepared by the following route by processes which are known per se from 4-acyloxyacetidin- 2-ones of the formula 12 or from sulphonylazetidin-2-ones of the formula 13:

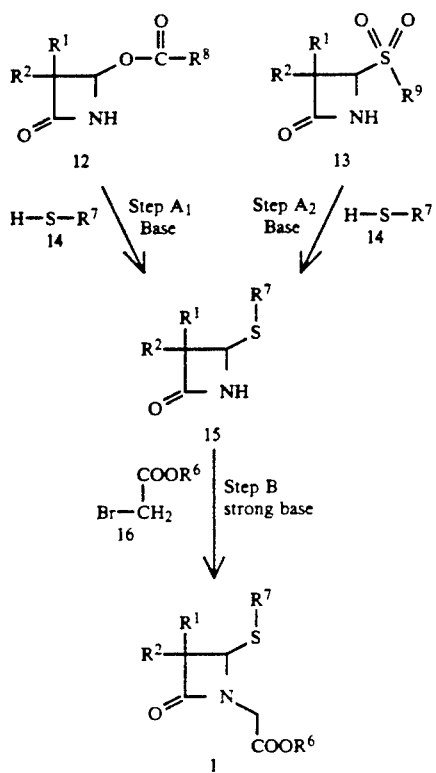

In which $R^1$, $R^2$, $R^7$ and $R^6$ have the abovementioned meanings and $R^8$ denotes an alkyl or aryl group, such as, for example, methyl or phenyl. $R^9$ is typically an alkyl or aryl group, such as, for example, methyl or phenyl, or a hydroxyalkyl or hydroxyaralkyl group, such as, for example, 2-hydroxyethyl, 2-hydroxyisopropyl, 2-hydroxy-1-phenylethyl or 2-hydroxy-1-tert-butyl or the like.

In the reaction (12→15) or (13→15), 12 or 13 respectively is reacted with 1–1.5 equivalents of a mercaptan (14) in a suitable solvent, such as tetrahydrofuran, tetrahydrofuran/H$_2$O or isopropanol/H$_2$O, in the presence of a base, such as diazabicycloundecene or sodium hydroxide solution or the like to form 15. The reaction temperature is typically −30° C. to room temperature and the reaction duration is typically about 30 minutes to 4 hours.

In the reaction (15→1), 15 is reacted with a suitable bromoacetate (16) in an inert solvent, such as tetrahydrofuran, dimethylformamide or a mixture of these solvents with hexane, in the presence of a strong base, such as butyllithium, potassium tert-butoxide, lithium diisopropylamide or lithium bis(trimethylsilylamide) or the like to form 1. Typical reaction temperatures are about −70°–0° C. and typical reaction times are 30 minutes to 2 hours.

Compounds 12 can be prepared from chlorosulphonyl isocyanate and vinyl esters according to Ann. Chem. 1974, 539, but syntheses which proceed from penicillin are also known (for example in Recent Advances in the Chemistry of β-Lactam Antibiotics, ed. by G. I. Gregory, The Royal Society of Chemistry, London, pages 330–348 (1981)). Compounds 13 can be prepared either from 12 in accordance with Ann. Chem. 1974, 539 or in accordance with Journ. Amer. Chem. Soc. 102, 2039 (1980) or Recent Adv. in the Chem. of β-Lactam Antibiotics, ed. by G. I. Gregory, The Royal Society of Chemistry, London, pages 368–378 (1981)), but processes for the preparation of 13 from penicillin are also known (for example Tetrahedron Lett. 22, 4141–4144 (1981)).

When chiral azetidinones 12 or 13 having the 4R configuration are used, compounds 1 having the same 4R configuration are produced.

The synthesis of the unsaturated starting material 7 is described below. 7 is expediently prepared in accordance with the following reaction equation:

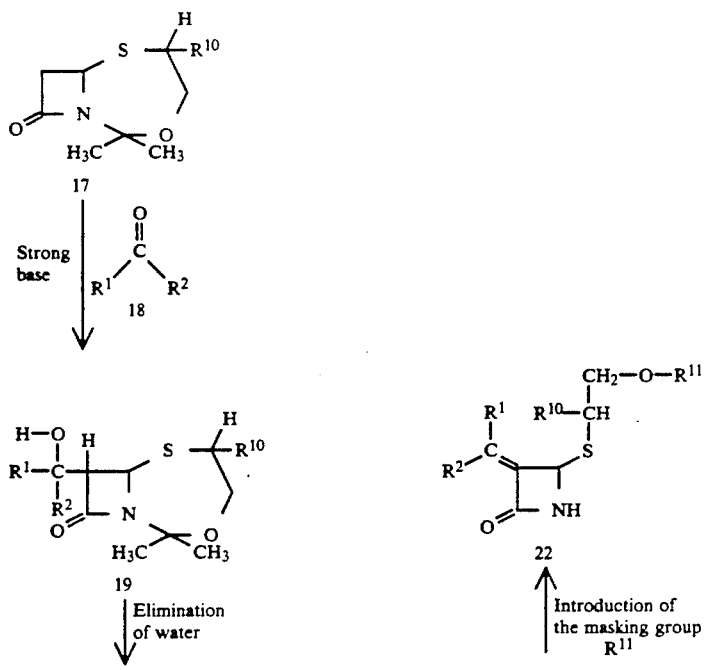

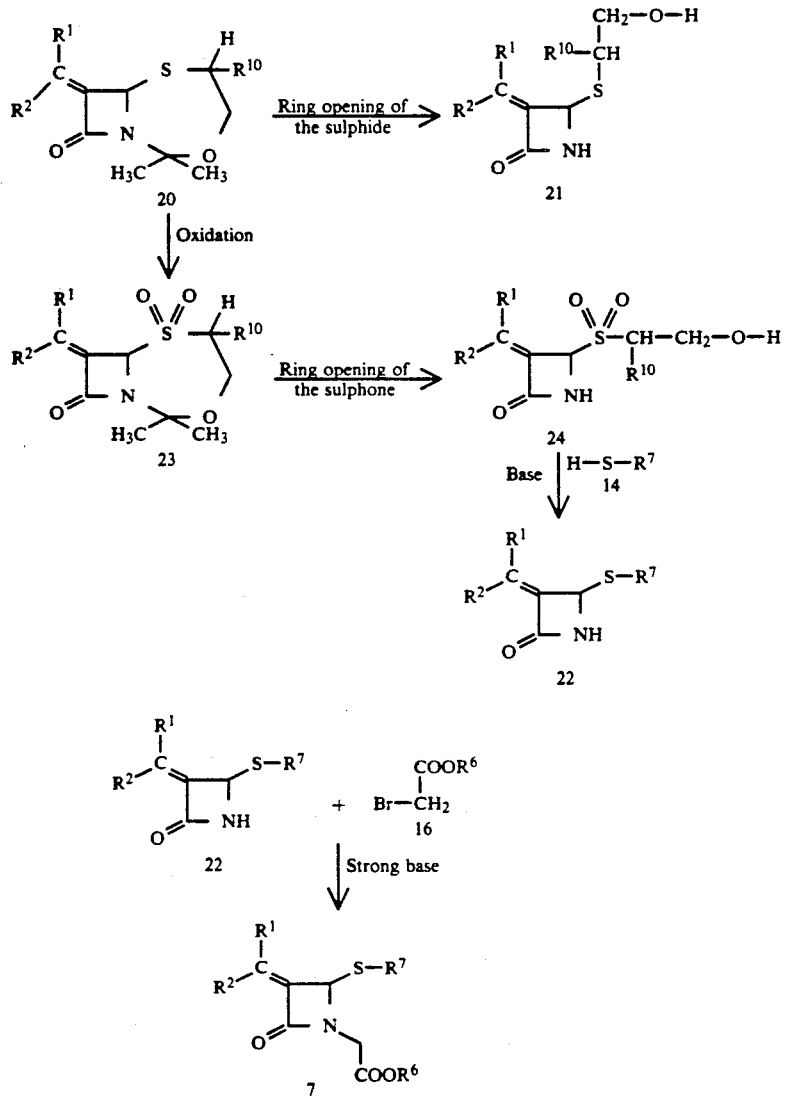

In which $R^1$, $R^2$, $R^6$ and $R^7$ have the abovementioned definitions, $R^{10}$ denotes hydrogen, an alkyl or aryl group, such as, for example, methyl or phenyl, and $R^{11}$ denotes a masking group which can easily be introduced, such as alkyl, aryl, aralkyl, acyl or trialkylsilyl. $R^{11}$ is typically benzyl, acetyl, benzoyl. trimethylsilyl or tert-butyldimethylsilyl or the like. However, the identity of the masking group is not particularly crucial since it need not be removed as such but nevertheless disappears again as part of an eliminated molecule at a later reaction stage, during the halogenation (8→9) or the cyclization using a mercury(II) salt (8→10).

In the reaction (17→19), 1 to 1.2 equivalents of a strong base, such as, for example, lithium diisopropylamide or the like, are added to 17 in an inert solvent, such as, for example, tetrahydrofuran or tetrahydrofuran/-hexane or the like, and the mixture is subsequently reacted with the ketone 18 to form 19. The reaction temperature is typically −70° C. to 0° C.; the reaction time is typically 30 minutes to 2 hours.

In the water elimination step (19→20), 1 to 1.5 equivalents of an acyl chloride, such as, for example, thionyl chloride, p-toluenesulphonyl chloride, methanesulphonyl chloride or acetyl chloride or the like, and 1 to 5 equivalents of a base, such as pyridine, triethylamine, N,N-dimethylaminopyridine or the like, are added to 19 in an inert solvent, such as, for example, tetrahydrofuran, and the ester intermediate is subsequently reacted with a strong base, such as potassium tert-butoxide or diazabicycloundecene or the like, in an inert solvent, such as, for example, tetrahydrofuran. The reaction temperatures in both reaction steps, i.e. in the esterification and in the elimination, are typically −30° C. to +50° C. The reaction duration in the esterification is 2 hours to 48 hours, depending on the base strength of the base used. The reaction duration in the elimination is about 30 minutes to 2 hours. The water elimination step proceeds more easily by heating 19 in an inert solvent, such as toluene or the like, on a water separator with the aid of a catalyst such as, for example, p-toluenesulphonic acid or p-toluenesulphonyl chloride. The reaction temperature is typically 2-10 hours at the reflux temperature of toluene.

In the ring-opening step of the sulphide (20→21), 20 is heated in an acid solvent, such as, for example, acetic acid/H$_2$O or the like. The reaction typically takes 30 minutes to 2 hours at the reflux temperature of about 110° C.

The masking group R[11] is introduced (21→22) by reacting 21 with 1 to 1.3 equivalents of a suitable alkylating or acylating agent which is easy to introduce, such as, for example, benzyl chloride, benzyl bromide, acetyl chloride, benzoyl chloride, trimethylchlorosilane or tert-butyldimethylchlorosilane, in the presence of a base, such as potassium tert-butoxide, triethylamine, N,N-di-methylaminopyridine, pyridine, imidazole or the like, in an inert solvent, such as tetrahydrofuran or dimethylformamide or the like. The reaction temperature is typically about −30° C. to room temperature.

The oxidation step (20→23) takes place by reacting 20 with an oxidant which is known per se and which can be used for sulphoxidation, such as, for example, potassium permanganate, hydrogen peroxide, m-chloroperbenzoic acid or the like. Typically, a solution of 20 in an inert solvent, such as, for example, methylene chloride, chloroform or acetone, is reacted with 2 to 2.5 equivalents of an oxidant, such as m-chloroperbenzoic acid, to form 23. The reaction temperature is typically −30° C. to room temperature and the reaction time is typically 30 minutes to 2 hours.

In the ring-opening step of the sulfone (23→24), 23 is heated in an acid solvent, such as, for example, acetic acid/H$_2$O or the like. The reaction typically takes 30 minutes to 20 hours at the reaction temperature of about 110° C.

Compounds of the formula 24 are then reacted with a mercaptan 14 in the presence of a base, such as, for example, sodium hydroxide solution and diazabicycloundecene or the like, to form 22. The reaction conditions correspond to those of reaction step (12→15).

Compounds of the formula 22 are reacted with a bromoacetate of the formula 16 with the aid of a strong base, such as, for example, butyllithium, lithium diisopropylamide or lithium bis-trimethylsilylamide, to form compound 7. The reaction conditions correspond to those of reaction step (15→1).

The compounds 17 are accessible by the method given in Recent Adv. in the Chem. of β-Lactam Antibiotics, ed. by G. I. Gregory, The Royal Society of Chemistry, London, pages 368–378 (1981) or Tet. Lett. 22, 4141–4144 (1981)). When a chiral starting material 17 having the 7R configuration is used, chiral 7 having the same 4R configuration is produced during the conversion (17→7).

In the general description of the present invention, the groups R[1] and R[2] are preferably selected from: hydrogen, alkyl, protected or unprotected hydroxyalkyl or protected or unprotected dihydroxyalkyl having up to 6 carbon atoms. R[3], R[4] and R[5] are preferably selected from substituted or unsubstituted alkyl, alkenyl, alkinyl, cycloalkyl, alkylcycloalkyl, alkylcylcoalkenyl, cycloalkylalkyl, alkenylcycloalkyl, cycloalkenylalkyl, aryl, aralkyl, aralkenyl, aralkinyl, carboxyl or cyano, where the foregoing alkyl, alkenyl or alkinyl molecule parts contain 1 to 6 carbon atoms, and the cycloalkyl or cycloalkenyl molecule parts contain 3 to 6 carbon atoms and the aryl molecule parts contain 6 to 10 carbon atoms, heteroaryl, heteroaralkyl, heteroaralkenyl, heteroaralkinyl, alkylheteroaryl, heterocyclyl, heterocyclylalkyl, heterocyclylalkenyl, heterocyclalkinyl or alkylheterocyclyl, where the foregoing alkyl, alkenyl or alkinyl molecule parts contain 1 to 6 carbon atoms and the heteroaromatic or heterocyclic molecule part is monocyclic or bicyclic and contains 3 to 10 ring atoms, of which one or more are selected from the series comprising: oxygen, sulphur and nitrogen, and where the substituents of the abovementioned groups may be: protected or unprotected hydroxyl, hydroxyalkoxy, aminoalkoxy, amidinoalkoxy, alkoxy, acyloxy, aryloxy, heteroaryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheteroarylthio, hydroxyalkylheteroarylthio, heterocyclylthio, carbamoylthio, alkylcarbamoylthio, thiocarbamoylthio or alkylthiocarbamoylthio, protected or unprotected amino or monoalkylamino, dialkylamino, oxo, protected or unprotected oximino or alkylamino, tetraalkylammonium, cycloalkylamino, arylamino, heteroarylamino, heterocyclylamino, acylamino, amidino, alkylamidino, guanidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents, independently of one another, occur once or several times and their alkyl molecule part contains 1 to 6 carbon atoms and their aryl molecule part contains 6 to 10 carbon atoms, and where the heteroaromatic or heterocyclic molecule part is monocyclic or bicyclic and contains 3 to 10 ring atoms, of which one or more are selected from the series comprising: oxygen, sulphur and nitrogen.

A particularly preferred class of compounds is that in which R[1] and R[2], independently of one another, denote hydrogen, alkyl, protected or unprotected hydroxyalkyl or protected or unprotected dihydroxyalkyl having up to 6 carbon atoms, R[3] and R[4] denote methyl, and R[5] is selected from the series comprising:

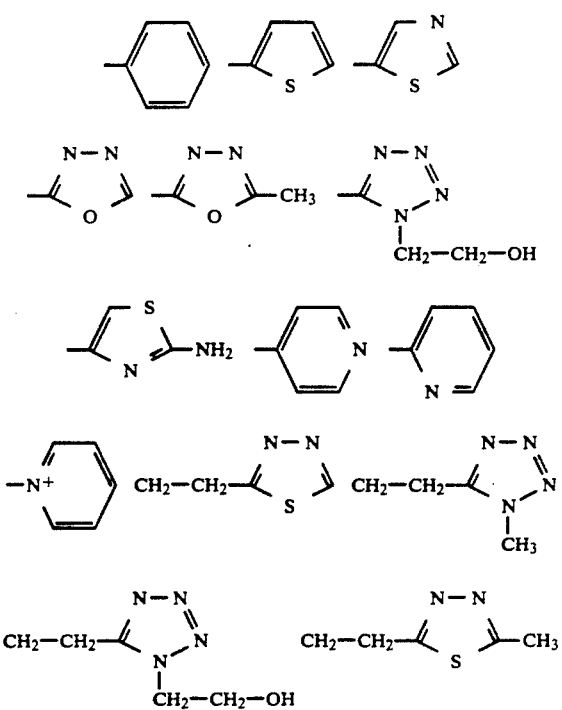

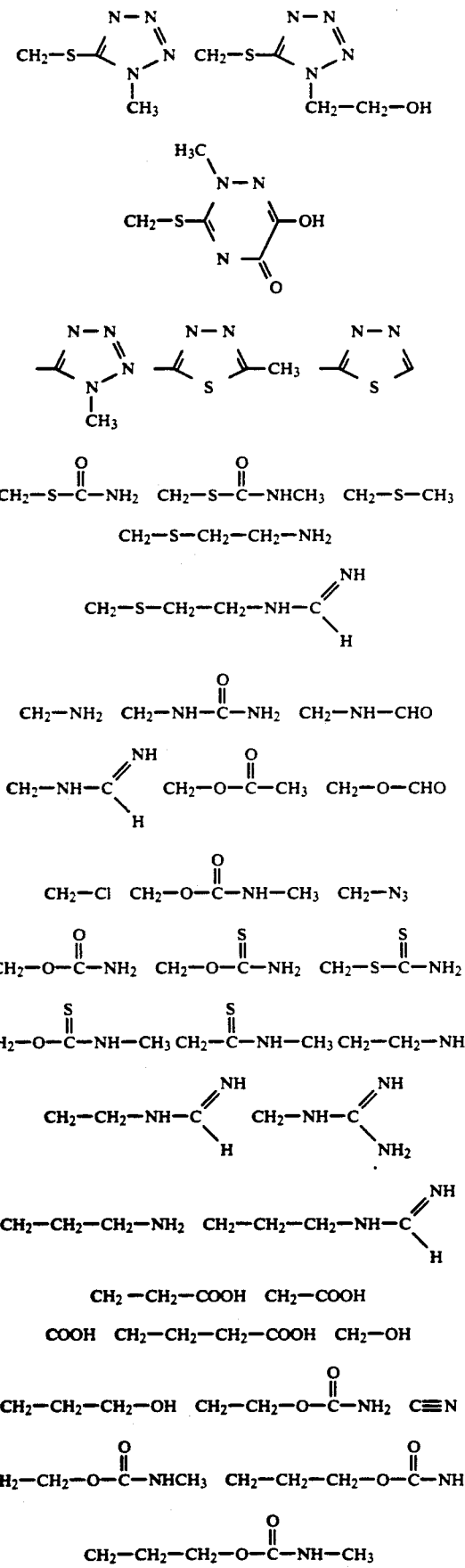

CH₂—CH₂—CH₂—NH—CHO.

Prefered esters used as protecting groups are those in which $R^6$ denotes benzyl, p-nitrobenzyl, methyl, tert-butyl, diphenylmethyl, trimethylsilyl, tert-butyldimethylsilyl or trichloroethyl; or $R^6$ denotes a pharmaceutically acceptable ester molecule part, such as pivaloyloxymethyl, allyl, methallyl, 2-oxoethyl, 2-oxopropyl, (2-methylthio)ethyl or 3-buten-1-yl.

Preferred protecting groups for the protected hydroxyalkyl and dihydroxyalkyl groups $R^1$ and $R^2$ are benzyl, p-nitrobenzyl, benzyloxycarbonyl p-nitrobenzyloxycarbonyl, trimethylsilyl, tert-butyldimethylsilyl, benzylidene and oxomethylene.

Preferred protecting groups for the protected substituents of $R^3$, $R^4$ and $R^5$ are identical to those mentioned above.

The products (I) and (II) according to the invention form a large number of pharmacologically acceptable salts with inorganic and organic bases. These include, for example, metal salts which are derived from alkali metal hydroxides, carbonates or bicarbonates, or alkaline earth metal hydroxides, carbonates or bicarbonates, and salts which are derived from primary, secondary or tertiary amines, such as monoalkylamines, dialkylamines, trialkylamines, lower alkanolamines, di(lower alkanolamines), lower alkylenediamines, N,N-diaralkyl(lower) alkylenediamines), aralkylamines, amino(substituted lower alkanols), N,N-di(lower alkylamino) (substituted lower alkanols), amino-, polyamino- and guanidino-(substituted lower alkanoic acids) and nitrogen-containing heterocyclic amine Examples of salts are those derived from sodium hydroxi sodium carbonate, sodium bicarbonate, potassium carbonate potassium hydroxide, calcium carbonate, trimethylamine, triethylamine, piperidine, morpholine, quinine, lysine, protamine, arginine, procaine, ethanolamine, morphine, benzylamine, ethylenediamine, N,N'-dibenzylethylenediamine, diethanolamine, piperazine, dimethylaminoethanol, 2-amino-2-methyl-1-propanol, theophylline, N-methylglucamine and the like.

The invention furthermore relates to salts of amino groups which are present in certain species I and II on the side chains of $R^3$, $R^4$ and $R^5$. Pharmaceutically acceptable acid addition salts of this type are derived from organic and inorganic acids, such as HCl, HBr, citric acid, tartaric acid, and the like.

The salts may be monosalts, such as the monosodium salt, which is obtained by treating 1 equivalent of sodium hydroxide with 1 equivalent of the products (I) and (II), or mixed disalts. Such salts can be obtained by treating 1 equivalent of a base with a divalent cation, such as calcium hydroxide, with 1 equivalent of the products (I) and (II). The salts according to the invention are pharmacologically acceptable, non-toxic derivatives which can be used as the active component in suitable pharmaceutical dose unit forms. They can also be combined with other medicaments to form preparations having a broad range of activity.

The new stable oxapen-2-em-carboxylic acids according to the invention are valuable antimicrobial substances which are active against various Gram-positive and Gram-negative pathogens. The free acid and, in particular, its salts, such as the amine and metal salts, in particular the alkali metal salts and alkaline-earth metal salts, are useful bactericides and can be employed to remove sensitive pathogens from dental and medical equipment, for removing microorganisms and for therapeutic use in humans and animals. For this latter purpose, pharmacologically acceptable salts with inorganic and organic bases, as are known per se and are used in the administration of penicillins and cephalosporins, are used. For example, salts, such as alkali metal salts and alkaline-earth metal salts, and primary, secondary and tertiary amine salts can be used for this purpose. These salts can be used together with pharmaceutically acceptable, liquid and solid excipients to form suitable dose unit forms, such as pills, tablets, capsules, suppositories, syrups, elixirs and the like, which can be prepared by processes which are known per se.

The new compounds are valuable antibiotics against various Gram-positive and Gram-negative bacteria and, accordingly, are used in human and veterinary medicine. The compounds according to the invention can be used as antibacterial medicaments for treating infections caused by Gram-positive or Gram-negative bacteria, for example against Staphylococcus aureus, Escherichia coli, Klebsisella pneumoniae, Bacillus subtilis, Salmonella typhosa, Pseudomonas and Bacterium proteus.

The antibacterial agents according to the invention can furthermore be used as additives for animal feeds, for preserving foodstuffs or feeds and as disinfectants. For example, they can be used in aqueous preparations in concentrations in the range 0.1 to 100 parts of antibiotic/million parts of solution for destroying and inhibiting the growth of harmful bacteria on medical and dental equipment and as bactericides in industrial applications, for example in water-based paints and in soft water for paper mills, or for inhibiting the growth of harmful bacteria.

The products according to the invention may be used alone or together as the active component in any of a large number of pharmaceutical preparations. These antibiotics and their corresponding salts can be used in capsule form or as tablets, powders or liquid solutions or as suspensions or elixirs. They can be administered orally, intravenously or intramuscularly.

The preparations are preferably administered in a form which is suitable for absorption through the gastrointestinal tract. Tablets and capsules for oral administration may be in dose unit form and can contain customary medicament excipients, such as binders, for example syrup, gum arabic, gelatin, sorbitol, tragacanth or polyvinylpyrrolidone; fillers, for example lactose, sugar, maize starch, calcium phosphate, sorbitol or glycine; lubricants, for example magnesium stearate, talc, polyethylene glycol or silicon dioxide; disintegrants, for example potato starch, or acceptable wetting agents, such as sodium lauryl sulphate. The tablets may be coated by processes which are well known per se. Oral liquid preparations can be in the form of aqueous or oily suspensions, solutions, emulsions, syrups, elixirs, etc., or can exist as dry product, for example for reconstitution before use using water or other suitable excipients. Liquid preparations of this type can contain additives which are known per se, such as suspending agents, for example sorbitol syrup, methylcellulose, glucose/sugar syrup, gelatin, hydroxyethylcellulose, carboxymethylcellulose, aluminium stearate gel, or hydrogenated edible oils, for example almond oil, fractionated coconut oil, oily esters, propylene glycol or ethyl alcohol; preservatives, for example methyl or propyl p-hydroxybenzoate or sorbic acid. Suppositories contain suppository bases which are known per se, for example cocoa butter or other glycerides.

The preparations for injection can be in dose unit form in ampules or in containers containing several doses along with an added preservative. The preparations can be in the form of suspensions, solutions or emulsions in oily or aqueous excipients, and they may contain formulation agents such as suspending agents, stabilizers and/or dispersants. Alternatively, the active component may be in powder form for reconstitution before use using a suitable excipient, for example sterile, pyrogen-free water.

The preparations can also be in suitable form for adsorption through the mucous membranes of the nose and of the throat or of the bronchial tissue, and can expediently be in the form of powders or liquid sprays or inhalants, sucking sweets, as throat paints, etc. For eye and ear medications, the preparations can be in the form of individual capsules in liquid or semi-solid form or they can be used as drops etc. topical applications can exist or be formulated in hydrophobic or hydrophilic vehicles as ointments, creams, lotions, paints, powders, etc.

The preparations according to the invention can contain, in addition to the excipient, another component, such as stabilizers, binders, antioxidants, preservatives, lubricants, suspending agents, viscosity-control agents or flavours or the like. In addition, the preparations may contain other active components so that a broader antibiotic range of activity is obtained.

For veterinary medicine, the preparations can be formulated, for example, as an intramammary preparation in either long-acting or rapid-release vehicles.

The dose to be administered is highly dependent on the state of the subject to be treated and the weight of the host, and on the method and frequency of administration. The parenteral route is preferred for generalized infections and the oral route for intestinal infections. In general, a daily oral dose contains about 15 to about 600 mg of active component/kg of body weight of the subject in case of one or more administrations per day. A preferred daily dose for adult humans is in the range about 40 to 120 mg of active component/kg of body weight.

The preparations according to the invention can be administered in various unit dose forms, for example in solid or liquid dose forms which can be taken orally. The preparations can contain 0.1 to 99% of active material per unit dose, either in solid or in liquid form. The preferred range is about 10 to 60%. The preparations generally contain 15 to about 1500 mg of active component but it is generally preferred to use a dose amount in the range about 250 to 1000 mg. In the case of parenteral administration, the unit dose is normally the pure compound in a sterile water solution or in the form of a soluble powder, which may be dissolved.

The examples below illustrate the products, processes, preparations and methods of treatment according to the invention.

EXAMPLE 1

Preparation of 2-tert-butyl-1-oxapen-2-em-3-carboxylic acid, the p-nitrobenzyl ester and the sodium salt thereof

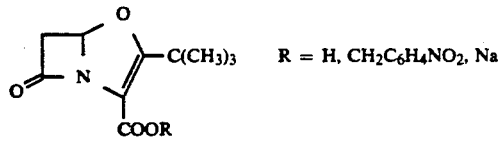    R = H, CH$_2$C$_6$H$_4$NO$_2$, Na

Step A$_1$: tert-Butylthioazetidin-2-one

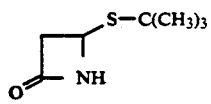

13.13 g of diazabicycloundecene (DBU) are added dropwise over the course of 35 minutes to a stirred solution of 9.689 g (75 mmol) of 4-acetoxyazetidin-2-one and 7.76 g (86 mmol) of tert-butyl mercaptan in 75 ml of dry THF at −3° C. at a rate such that the reaction temperature does not exceed −1.5° C. The mixture is stored overnight at 0° C. and then stirred for a further 1½ hours at room temperature. The mixture is diluted with 500 ml of methylene chloride and washed with 100 ml of saturated aqueous sodium chloride solution, 100 ml of 2N hydrochloric acid and a further 100 ml of sodium chloride solution, the organic phase is dried over magnesium sulphate, and the solvent is evaporated in vacuo to give a solid residue which is chromatographed over 300 g of silica gel using toluene:ethyl acetate 2:1. After recrystallizing the chromatographed product from methylene chloride/hexane, 6.5 g of pure title compound of melting point 119°–121° C. are obtained. IR spectrum in methylene chloride: 3410, 2955, 2905, 2865, 1770, 1460, 1410, 1370, 1340, 1160, 970, 925 cm$^{-1}$.

Alternative preparation of tert-butylthioazetidin-2-one from 4-benzoyloxyazetidin-2-one 41.25 ml (82.5 mmol) of 2N NaOH in water are added dropwise to a solution of 9.3 ml (82.5 mmol) of tert-butyl mercaptan in 37.5 ml of acetonitrile at 0° C. A solution (warm!) of 14.32 g (75 mmol) of 4-benzoyloxyazetidin-2-one in 56 ml of acetonitrile is then added dropwise over the course of 25 minutes at a rate such that the reaction temperature does not exceed 0° C. The precipitate produced as an intermediate during the dropwise addition dissolves completely on further stirring at 0° C. The mixture is then left to stand at 0° C. overnight, thin-layer chromatography on silica gel using toluene:ethyl acetate (1:1) indicating that starting material is no longer present. 500 ml of methylene chloride are added to the yellow reaction solution, and the aqueous phase is separated off and again extracted with 100 ml of methylene chloride. The combined extraction solutions are washed successively with 100 ml in each case of 1N HCl solution, twice with NaHCO$_3$ solution and once with dilute NaCl solution. The organic phase is dried over MgSO$_4$ and filtered, and the solvent is evaporated in vacuo to give 11.8 g (99%) of a yellow crystalline residue. Recrystallization from 160 ml of dibutyl ether at 90° C.→0° C. gives 10.3 g (86%) of pure title compound of melting point 119°–120° C.

Step B:

p-Nitrobenzyl (4-tert-butylthio-2-oxo-1-azetidinyl)acetate

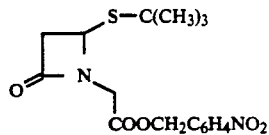

14.4 ml of a 1N solution of lithium bistrimethylsilylamide in tetrahydrofuran (THF) are added dropwise to a stirred solution of 1.91 g (12 mmol) of tert-butylthioazetidin-2-one in 6 ml of dry N,N-dimethylformamide (DMF) at −70° C., and a solution of 4.93 g (18 mmol) of p-nitrobenzyl bromoacetate in 6 ml of DMF is subsequently added dropwise to the mixture, and the mixture is then stirred for a further 30 minutes at −30° C. The reaction mixture is diluted with 100 ml of toluene and washed with three 50 ml portions of water, the organic phase is dried over magnesium sulphate, and the solvent is evaporated in vacuo to give 4.3 g of a solid crude product, which is chromatographed over 120 g silica gel using toluene:ethyl acetate (4:1). The purified product (2.6 g) is recrystallized from 100 ml of dry isopropanol. Yield 2.09 g of melting point 82.5°–84° C. IR spectrum in methylene chloride: 2955, 1770, 1755, 1610, 1530, 1390, 1375, 1365, 1345, 1180, 1110, 945, 915, 855, 845 cm$^{-1}$.

Step C:

p-Nitrobenzyl 2-(4-tert-butylthio-2-oxo-1-azetidinyl)-4,4-dimethyl-3-oxopentanoate

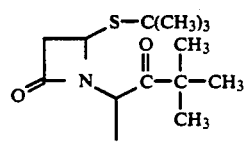

6 ml of a freshly prepared 1M solution of lithium bis-trimethysilylamide in THF are added dropwise to a solution of 1059 mg (3 mmol) of p-nitrobenzyl (4-tert-butylthio-2-oxo-1-azetidinyl)acetate in 7 ml of dry THF at −70° C., and a solution of 382 mg of pivaloyl chloride in 1 ml of THF is subsequently added dropwise at −70° C., and the reaction mixture is then stirred for 30 minutes at the same temperature. The mixture is diluted with 200 ml of toluene and a little aqueous acetic acid is added. The organic phase is washed with 100 ml of 2N aqueous hydrochloric acid and twice with saturated sodium chloride solution (100 ml), the organic phase is dried using MgSO$_4$, and the solvent is evaporated in vacuo to give a dark red oil. Purification of the crude product over 40 g of silica gel using toluene: ethyl acetate (9:1) gives 795 mg of a non-crystalline solid. IR spectrum in methylene chloride: 2970, 1770, 1760, 1715, 1610, 1530, 1370, 1350, 1315, 1180, 995, 845 cm$^{-1}$.

Step D₁:

p-Nitrobenzyl 2-(4-chloro-2-oxo-1-azetidinyl)-4,4-dimethyl-3-oxopentanoate

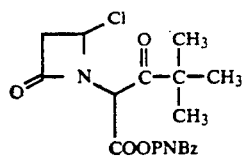

A solution of 439 mg (1.0 mmol) of p-nitrobenzyl 2-(4-tert-butylthio-2-oxo-1-azetidinyl)-4,4-dimethyl-3-oxopentanoate in 20 ml of dry methylene chloride is cooled to −50° C. and a solution of 166 mg of chlorine in 1.6 ml of carbon tetrachloride is added. After stirring the mixture for thirty minutes at −50° C., the solvent is evaporated in vacuo and the residue is recrystallized from methylene chloride/hexane, the product (348 mg) being obtained as a crystalline solid as a 6:4 mixture of the diastereomeric title compounds.

Melting point 96°-100.5° C., decomposition.

¹H-NMR (CD₃CN): $\delta = 1.04$ (s, ~5.4 H, t-butyl I), 1.21 (s, ~3.6 H, t-butyl II), 3.05-3.86 (m, 1H, 3'-H), 5.29 (s, 2H, -O-CH₂-Ar), 5.52 (s, ~0.6 H, 2-H, I), 5.71 (s, ~0.4, 2-H, II), 5.84 (dd, J=2 Hz, J=4 Hz ~0.6 H 4'-H, I), 5.98 (dd, J=2 Hz, J=4 Hz, ~0.4 H, 4'-H, II), 7.51 (d, J=9 Hz, ~0.8 H, Ar-H, II), 7.55 (d, J=9 Hz, ~1.2 H, Ar-H, I), 8.19 (d, J=9 Hz, 2 H, Ar-H, I and II).

Step D₂:

p-Nitrobenzyl 3-tert-butyl-7-oxo-4-oxa-1-azabicyclo[3.2.0]hept-2-ene-2-carboxylate

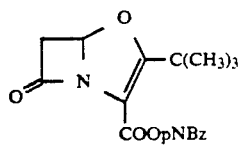

The mixture of diastereomeric p-nitrobenzyl 2-(chloro-2-oxo-1-azetidinyl)-4,4-dimethyl-3-oxopentanoates (348 mg, 0.91 mmol) was dissolved in dry THF (10 ml), and 0.91 ml of a freshly prepared 1M solution of potassium tert-butoxide in tert-butanol was added at 0° C., the reaction mixture was stirred for 15 minutes at 0° C. The mixture was diluted with 150 ml of benzene, and washed three times with 50 ml of 0.5M phosphate buffer solution pH=7 in each case, the organic phase was dried over MgSO₄, and the solvent was evaporated in vacuo to give a pale yellow solid, which is chromatographed over 9 g of silica gel using benzene:ethyl acetate 97:3 to give 237 g of product. Recrystallization from methylene chloride/hexane gives 200 mg of pale yellow crystals of melting point 142°-144° C.

¹H-NMR (CD₃CN): $\delta = 1.29$ (s, 9 H, tert-butyl), 3.40 (dd, J=17 Hz, J=1 Hz, 1 H, 6-H trans), 3.79 (dd, J=17 Hz, J=2.5 Hz, 1 H, 6-H cis), 5.16 (d, J=14 Hz, 1H, -O-CH₂-Ar), 5.42 (d, J=14 Hz, 1 H, -O-CH₂-Ar), 5.85 (dd, J=2.5 Hz, J=1 Hz, 1 H, 5-H), 7.61 (d, J=8.5 Hz, 2 H, Ar—H), 8.17 (d, J=8.5 Hz, 2 H, Ar—H). IR spectrum in methylene chloride: 2955, 1804, 1715, 1610, 1585, 1525, 1350, 1315, 1200, 1165, 1145, 1120, 1080, 1040, 1025, 1015, 885, 855, 840 cm⁻¹. UV spectrum in dioxane: $\lambda_{max} = 277$ nm ($\epsilon = 15340$).

Step E:

3-tert-Butyl-7-oxo-4-oxa-1-azabicyclo[3.2.0]hept-2-ene-2-carboxylic acid, Na salt

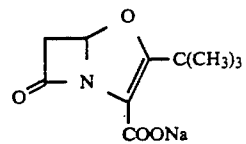

A solution of 17.3 mg (50 μmol) of p-nitrobenzyl 3-tert-butyl-7-oxo-4-oxa-1-azabicyclo[3.2.0]hept-2-ene-2-carboxylate in 1 ml of ethyl acetate are injected through a septum stopper into a mixture, cooled to 0° C., of 30 mg of palladium on charcoal (10%), 2 ml of ethyl acetate and a solution of 4.7 mg (56 μmol) of sodium hydrogen carbonate in 1 ml of water under a hydrogen atmosphere, and the mixture is hydrogenated. 5.4 ml of hydrogen, somewhat more than the theoretically necessary amount (4.6 ml), are consumed within 20 minutes. The multiphase mixture is filtered while cooling, and the cooled (0° C.) filtrate is washed twice with 3 ml of ethyl acetate in each case. The aqueous solution is immediately lyophilized in a high vacuum to give 8.8 mg of a white solid. UV (H₂O): $\lambda_{max} = 269$ nm ($\epsilon = 5800$) 360 MHz - ¹H-NMR spectrum in D₂O: $\delta = 1.23$ (s, 9 H, tert-butyl), 3.43 (dd, J=18 Hz, J=1 Hz, 1 H, 6-H trans), 3.72 (dd, J=18 Hz, J=2.5 Hz, 1 H, 6-H cis), 5.82 (s, 1 H, 5-H).

EXAMPLE 2

Preparation of 2-tert-butyl-6-methyl-1-oxapen-2-em-3-carboxylic acid, the p-nitrobenzyl ester and its sodium salt

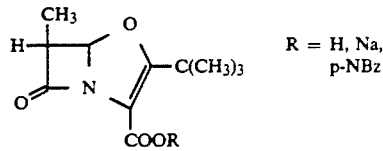

R = H, Na, p-NBz

By the process described in Example 1 using the same reaction conditions and starting from 4-acetoxy-3-methylazetidin-2-one via steps A₁, B and C, p-nitrobenzyl 2-(4-tert-butylthio-3-methyl-oxo-1-azetidinyl)-4,4-dimethyl-3-oxopentanoate

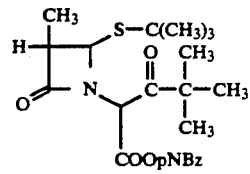

is obtained as a non-crystalline solid. IR spectrum in methylene chloride: 2955, 1765, 1760, 1720, 1610, 1525, 1460, 1380, 1365, 1350, 1315, 1205, 1180, 1120, 1050, 855, 840 cm⁻¹. UV spectrum in ethanol: $\lambda_{max} = 264$ nm ($\epsilon = 10160$).

Step D₁:

p-Nitrobenzyl 2-(4-chloro-3-methyl-2-oxo-1-azetidinyl)-4,4-dimethyl-3-oxopentanoate

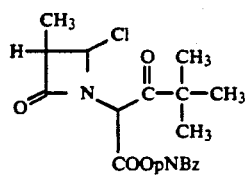

By the process described in Example 1 using the same reaction conditions and starting from p-nitrobenzyl 2-(4-tert-butylthio-3-methyl-2-oxo-1-azetidinyl)-4,4-dimethyl-3-oxopentanoate, the title compound (step D₁) is obtained as a non-crystalline solid (mixture of two diastereomers). NMR spectrum in DC₃CN: δ=1.19, 1.21 and 1.32 (3 signals, 12 H), 3.59–3.98 (m, 1 H), 5.30 (s, 2 H), 5.50 (s, ~0.25 H), 5.70 (s, ~0.75 H), 5.94 (d, J=5 Hz, ~0.25 H), 6.09 (d, J=5 Hz, ~0.75 H), 7.43–7.64 (m, 2 Hz) 8.17 (d, J=9 Hz, 2 H).

Step D₂:

p-Nitrobenzyl 2-tert-butyl-6-methyl-1-oxapen-2-em-3-carboxylate (p-nitrobenzyl 3-tert-butyl-7-oxo-4-oxa-1-azabicyclo[3.2.0]hept-2-ene-2-carboxylate

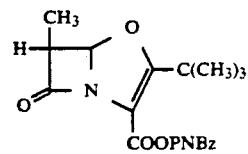

By the process described in Example 1 using the same reaction conditions and starting from p-nitrobenzyl 2-(4-chloro-3-methyl-2-oxo-1-azetidinyl)-4,4-dimethyl-3-oxopentanoate, the title compound was obtained as a noncrystalline solid (mixture of cis/trans isomers). IR spectrum in CH₂Cl₂: 2965, 1800, 1715, 1585, 1525, 1345, 1310, 1165, 1140, 1085, 1025, 1015, 935, 850 cm⁻¹. UV spectrum in dioxane: λ$_{max}$=277 nm (ε=15200).

Step E:

3-tert-Butyl-6-methyl-7-oxo-4-oxa-azobicyclo[3.2.0]hept-2-ene-2-carboxylic acid, Na salt

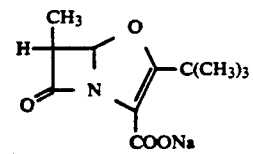

By the process described in Example 1 using the same reaction conditions and starting from p-nitrobenzyl 3-t-butyl-6-methyl-7-oxo-4-oxa-1-azabicyclo[3.2.0]hept-2-ene-2-carboxylate, the title compound was obtained as a white solid (lyophilisate). UV spectrum in H₂O: λ$_{max}$=260 nm (ε=5800). ¹H-NMR-spectrum in D₂O: 1.24 and 1.27 (2s, 9 H), 1.38 (d, J=7.5 Hz), 3.67 (q, J=7.5 Hz), ~0.5 H, trans), 3.96 (dq, J=7.5 Hz, J=3 Hz, ~0.5 H, cis), 5.55 (s, ~0.5 H, trans), 5.80 (d, J=3 Hz, ~0.5 Hz, cis).

EXAMPLE 3

Preparation of 2-tert-buty-6,6-dimethyl-1-oxapen-2-em-3-carboxylic acid, the p-nitrobenzyl ester and its sodium salt

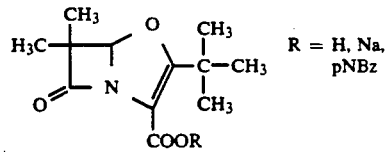

R = H, Na, pNBz

By the process described in Example 1 using the same reaction conditions and starting from 4-acetoxy-3,3-dimethylazetidin-2-one via steps A₁, B and C, p-nitrobenzyl 2-(4-tert-butylthio-3,3-dimethyl-2-oxo-1-azetidinyl)-4,4-dimethyl-3-oxopentanoate

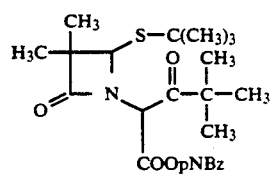

was obtained as a crystalline solid of melting point 87.5°–90.5° C. from methylene chloride/hexane (mixture of two diastereomers). IR spectrum in methylene chloride: 2955, 2865, 1765, 1755, 1715, 1610, 1525, 1460, 1390, 1370, 1350, 1315, 1185, 1135, 1105, 995, 850 cm¹⁻. UV spectrum in ethanol: λ$_{max}$=264.5 nm (ε=10930).

Step D:

p-Nitrobenzyl 3-tert-butyl-6,6-dimethyl-7-oxo-4-oxa-1-azabicyclo[3.2.0]hept-2-ene-2carboxylate

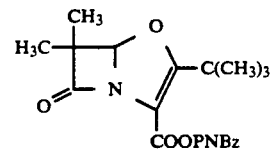

A solution of 930 mg (2.0 mmol) of p-nitrobenzyl 2-(4-tert-butylthio)-3,3-dimethyl-2-oxo-1-azetidinyl)-4,4-dimethyl-3-oxopentanoate in 460 ml of dry dimethoxyethane was stirred vigorously together with 1046 mg (5.0 mmol) of yellow mercury(II) oxide and 1358 mg (5.0 mmol) of mercury(II) chloride, and the mixture was refluxed for 3 hours. After cooling, the yellowish solution was filtered through Cellite and concentrated to about a tenth of the volume. The mixture was diluted with 500 ml of benzene and left to stand for 2 days at 0° C., the colourless precipitate produced was then filtered off, and the clear solution obtained was washed with 250 ml of saturated sodium chloride solution, 250 ml of 0.5M of phosphate buffer solution pH 7 and 250 ml of saturated sodium chloride solution. The organic phase is dried using magnesium sulphate, the solution is concentrated to 50 ml and left to stand at 0° C., the small amount of precipitate which re-deposits is filtered off, and the solvent is stripped off in vacuo to give a yellow, slightly turbid oil. Chromatography of the crude product over 25 g of Florisil using benzene:ethyl acetate (7:1) gave 560 mg of pure title compound. After recrystallization from methylene chloride/hexane, the melting point was 119°-120.5° C.

IR spectrum in methylene chloride: 2935, 2870, 1797, 1715, 1610, 1585, 1525, 1460, 1350, 1315, 1155, 1140, 1085, 1010, 850 cm$^{-1}$, UV spectrum in dioxane: $\lambda_{max}$=278 nm ($\epsilon$=14980). Mass spectrum (20 eV, 80° C.): 374 M$^+$. An X-ray structural analysis was carried out for this substance and confirmed the structure.

Step E:

3-tert-Butyl-6,6-dimethyl-7-oxo-4-oxa-1-azabicyclo[3.2.0]hept-2-ene-2-carboxylic acid, Na salt

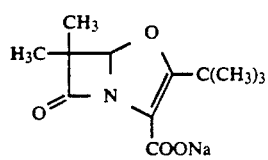

By the process described in Example 1 using the same reaction conditions and starting from p-nitrobenzyl 3-tert-butyl-6,6-dimethyl-7-oxo-4-oxa-1-azabicyclo[3.2.0]-hept-2-ene-2-carboxylate, the title compound was obtained as a pale yellow solid (lyophilisate). UV spectrum in H$_2$O: $\lambda_{max}$=261 nm. NMR spectrum in D$_2$O: 1.23 (s, 9 H), 1.26 (s, 3 H), 1.39 (s, 3 H), 5.50 (s, 1 H).

EXAMPLE 4

Preparation of 2-(2-Chloro-1,1-dimethylethyl)-6,6-dimethyl-1-oxapen-2-em-2-carboxylic acid, the p-nitrobenzyl ester and its Na salt

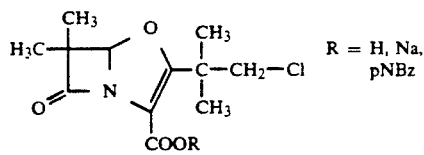

By the process described in Example 3 using the same reaction conditions and starting from 4-acetoxy-3,3-dimethylazetidin-2-one and using chloropivaloyl chloride in step C via steps A$_1$, B, C and D, the compound

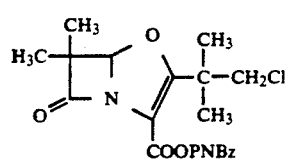

was obtained as a non-crystalline solid. IR spectrum in methylene chloride: 2930, 2875, 1803, 1710, 1590, 1525, 1460, 1370, 1350, 1315, 1255, 1160, 1130, 1115, 1090, 1010, 990, 920, 850 cm$^{-1}$.

Step E:

3-(2-Chloro-1,1-dimethylethyl)-6,6-dimethyl-7-oxo-4-oxa-1-azabicyclo[3.2.0]hept-2-ene-2-carboxylic acid, Na salt

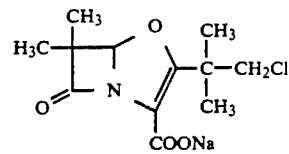

By the process given in Example 3 starting from the appropriate p-nitrobenzyl ester, the title compound was obtained in 60% yield as a non-crystalline colourless solid after lyophilization. NMR spectrum in D$_2$O: $\delta$=1.27, 1.30, 1.33 and 1.39 (4s, 12 H), 3.74 (d, J=10 Hz, 1 H), 4.05 (d, J=10 Hz, 1 H), 5.52 (s, 1 H). UV spectrum in H$_2$O: $\lambda_{max}$=265 nm ($\epsilon$=5800).

EXAMPLE 5

Preparation of 6,6-dimethyl-3-(1-methyl-1-phenylethyl)-7-oxo-4-oxa-1-azabicyclo[3.2.0]hept-2-ene-2-carboxylic acid, its Na salt and its p-nitrobenzyl ester

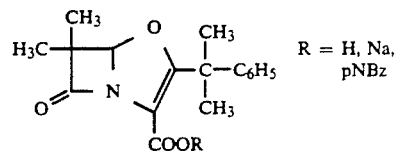

By the process described in Example 1 starting from p-nitrobenzyl 2-(4-tert-butylthio-3,3-dimethyl-2-oxo-azetidinyl)acetate and 2-methyl-2-phenylpropionyl chloride via steps C, D$_1$ and D$_2$, the title compound (p-nitrobenzyl ester) was obtained as a non-crystalline, slightly yellowish solid. IR spectrum in CH$_2$Cl$_2$: 2930, 2875, 1800, 1720, 1600, 1525, 1350, 1320, 1145, 1085, 1075 cm$^{-1}$.

Step E:

6,6-Dimethyl-3-(1-methyl-1-phenylethyl)-7-oxo-4-oxa-1-azabicyclo[3.2.0]hept-2-ene-2-carboxylic acid, Na salt

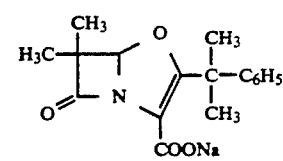

By the process described in Example 1 starting from the appropriate p-nitrobenzyl ester, the title compound was obtained in a 50% yield as a colourless solid after lyophilization. UV spectrum in H$_2$O: $\lambda_{max}$=263 nm ($\epsilon$=5600).

EXAMPLE 6

Preparation of
6,6-dimethyl-3-(1,1-diphenylethyl)-7-oxo-4-oxa-1-azabicyclo[3.2.0]hept-2-ene-2-carboxylic acid, its Na salt and its p-nitrobenzyl ester

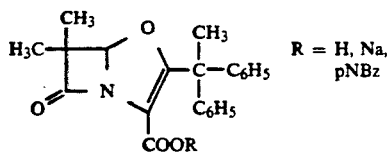

R = H, Na, pNBz

By the process described in Example 1 starting from p-nitrobenzyl 2-(4-tert-butylthio)-3,3-dimethyl-2-oxoazetidinyl)acetate and 2,2-diphenylpropionyl chloride, via steps C, D₁ and D₂, the title compound (p-nitrobenzyl ester) was obtained as a colourless solid. IR spectrum in CH₂Cl₂: 2930, 2875, 1805, 1725, 1600, 1525, 1350, 1315, 1150, 1085, 1075 cm⁻¹.

Step E:

6,6-Dimethyl-3-(1,1-diphenyl ethyl)-7-oxo-4-oxa-1-azabicyclo[3.2.0]hept-2-ene-2-carboxylic acid, Na salt

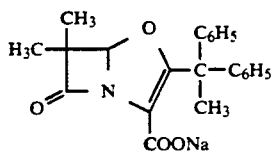

By the process described in Example 1 starting from the appropriate p-nitrobenzyl ester, the title compound was obtained in 63% yield as a colourless solid after lyophilization. UV spectrum in H₂O: λ_max=265 nm (ε=6000).

EXAMPLE 7

Preparation of
6,6-dimethyl-3-[1-methyl-1-(2-thienyl)ethyl]-7-oxo-4-oxa-1-azabicyclo[3.2.0]hept-2-ene-2-carboxylic acid, its Na salt and its p-nitrobenzyl ester

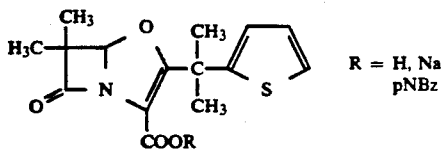

R = H, Na pNBz

By the process described in Example 1 starting from p-nitrobenzyl 2-(4-tert-butylthio-3,3-dimethyl-2-oxoazetidinyl)acetate and 2-methyl-2-thienylpropionyl chloride via steps C, D₁ and D₂, the title compound (p-nitrobenzyl ester) was obtained as a slightly yellowish solid. IR spectrum in CH₂Cl₂: 2930, 1795, 1715, 1590, 1520, 1350, 1310, 1140, 1080 cm⁻¹.

Step E:

6,6-Dimethyl-3-[1-methyl-1-(2-thienyl)ethyl]-7-oxo-4-oxa-1azabicyclo[3.2.0]hept-2-ene-2-carboxylic acid, Na salt

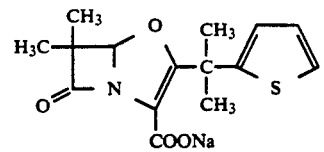

By the process described in Example 1 starting from the appropriate p-nitrobenzyl ester, the title compound was obtained in a 70% yield as a colourless non-crystalline solid (lyophilisate). UV spectrum in H₂O: λ_max=270 nm (ε=6500).

EXAMPLE 8

Preparation of
3-(2-amino-1,1-dimethylethyl)-7-oxo-4-oxa-1-bicyclo[3.2.0]hept-2-ene-2-carboxylic acid

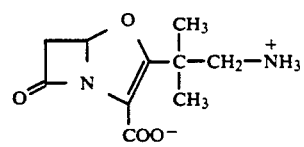

Step C:

p-Nitrobenzyl
2-(4-tert-butylthio-2-oxo-1-aze-tidinyl)-5-chloro-4,4-dimethyl-3-oxopentanoate

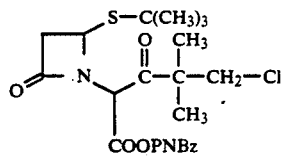

6 ml of a 1M solution of lithium bis(trimethylsilylamide) in THF is slowly added dropwise to a stirred mixture, at 70° C., of 1.06 g (3 mmol) of p-nitrobenzyl 2-(4-tertbutylthio-2-oxo-1-azetidinyl)acetate and 410 μl (3.17 mmol) of chloropivaloyl chloride in 38 ml of absolute tetrahydrofuran, and the mixture is stirred for a further 30 minutes at −70° C. The reaction mixture is diluted with 250 ml of toluene, and 10 ml of 2N aqueous HCl and 100 ml of saturated NaCl solution are added. After separation, the organic phase is again washed with 100 ml of saturated NaCl solution then dried over MgSO₄, and filtered, and the solvent is removed in vacuo on a rotary evaporator. The non-crystalline residue is chromatographed over 46 g of silica gel using toluene:ethyl acetate (19:1), to give 980 mg of non-crystalline title compound. IR in CH₂Cl₂: 2930, 1770, 1760, 1725, 1615, 1530, 1465, 1370, 1250, 1215, 1190, 1110, 1040, 1000, 847 cm⁻¹.

Conversion of a group R³; p-nitrobenzyl 5-azido-2-(4-tert-butylthio-2-oxo-1-azetidinyl)-4,4-dimethyl-3-oxopentanoate

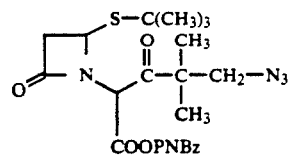

A mixture of 236 mg (0.5 mmol) of p-nitrobenzyl 2-(4-tert-butylthio-2-oxo-1-azetidinyl)-5-chloro-4,4-dimethyl-3-oxopentaonate and 200 mg (1.04 mmol) of Triton B acid in 0.3 ml of DMF is stirred for 20 hours at room temperature, then diluted with toluene and washed twice with water. The aqueous phase is extracted with a little toluene, and the combined organic phases are dried over MgSO₄. Filtration and evaporation of the residue in vacuo gives 290 mg of a colourless residue. IR spectrum in CH$_2$Cl$_2$: 2930, 2860, 2110, 1775, 1755, 1720, 1610, 1530, 1350, 1180, 1120, 850 cm⁻¹.

Step D₁:

p-Nitrobenzyl 5-azido-2-(4-chloro-2-oxo-1-azetidinyl)-4,4-dimethyl-3-oxopentanoate

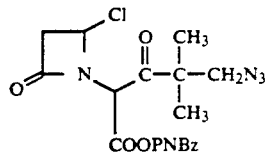

286 µl of a solution containing 1.14 g/10 ml of chlorine in carbon tetrachloride are added to a solution of 110 mg of p-nitrobenzyl 5-azido-2-(4-tert-butylthio-2-oxo-1-azetidinyl)-4,4-dimethyl-3-oxopentanoate in 9 ml of methylene chloride at −60° C., and the mixture is subsequently stirred for 2 hours at −60° C. The reaction solution is evaporated in a rotary evaporator to give 119 mg of a yellow oil. IR spectrum in CH$_2$Cl$_2$: 2930, 2860, 2105, 1780, 1755, 1720, 1610, 1530, 1350, 1190 cm⁻¹.

Step D₂:

p-Nitrobenzyl 3-(2-azido-1,1-dimethylethyl)-7-oxo-4-oxa-1-azabicyclo[3.2.0]hept-2-ene-2-carboxylate

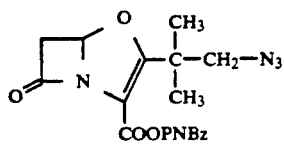

313 µl of a 0.75M solution of potassium tertbutoxide in tert-butanol are added to a solution of 107 mg (0.23 mmol) of 5-azido-2-(4-chloro-2-oxo-1-azetidinyl)-4,4-dimethyl-3-oxopentanoate in 4.5 ml of dry tetrahydrofuran at −30° C., and the solution is stirred at −30° C. for 30 minutes. The reaction mixture is then diluted with 20 ml of ethyl acetate and washed with 10 ml of water and 10 ml of NaCl solution. The aqueous phases are extracted with 10 ml of ethyl acetate, and the combined organic phases are dried over MgSO₄, filtered and then evaporated in vacuo. 105 mg of a yellow residue are obtained, which is crystallized from methylene chloride/diisopropyl ether. Yield 61 mg of melting point 81°-82° C. IR spectrum in CH$_2$Cl$_2$: 2950, 2860, 2110, 1810, 1720, 1590, 1530, 1370, 1320, 1085, 1020 cm⁻¹.

Step E:

3-(2-Amino-1,1-dimethylethyl)-7-oxo-4-oxa-1-azabicyclo[3.2.0]hept-2-ene-2-carboxylic acid

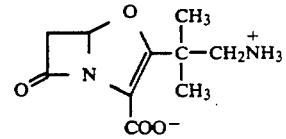

A solution of 21 mg (0.054 mmol) of p-nitrobenzyl 3-(2-azido-1,1-dimethylethyl)-7-oxo-4-oxa-1-azabicyclo[3.2.0]hept-2-ene-2-carboxylate in 1 ml of ethyl acetate is added via a syringe through a septum stopper to a prehydrogenated mixture, at 0° C., of 60 mg of palladium on charcoal (10%) in 1 ml of ethyl acetate and 0.7 ml of water. After a reaction time of 20 minutes, 5.7 ml of hydrogen have been taken up (theoretical amount 4.9 ml). The reaction mixture is filtered at 0° C., and the aqueous phase is washed twice with 2 ml of pre-cooled ethyl acetate. The aqueous phase contains 8.96 mg of the title compound. UV spectrum in H$_2$O: $\lambda_{max}$=271 nm ($\epsilon$=5000)

EXAMPLE 9

Preparation of 3-[1,1-dimethyl-2-((1-methyl-1,2,3,4-tetrazol-5-yl)-thio)-ethyl]-7-oxo-4-oxa-1-azabicyclo[3.2.0]-hept-2-enecarboxylic acid, its Na salt and its p-nitrobenzyl ester

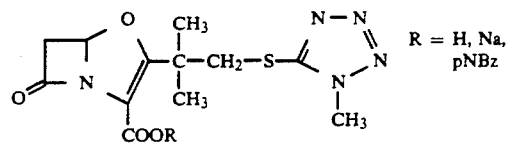

Conversion of a group R³; p-nitrobenzyl 2-(4-tert-butylthio-2-oxo-1-azetidinyl)-4,4-dimethyl-5-[(1-methyl-1,2,3,4-tetrazol-5-yl)-thio]-3-oxopentanoate

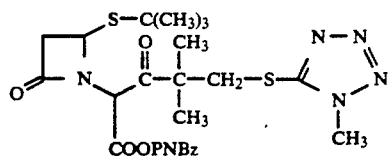

A mixture of 118 mg (0.25 mmol) of p-nitrobenzyl 2-(4-tert-butylthio-2-oxo-1-azetidinyl)-5-chloro-4,4-dimethyl-3-oxopentanoate and 82 mg (0.59 mmol) of the Na salt of 1-methyl-5-mercapto-1,2,3,4-tetrazole are stirred for 20 hours at room temperature in 0.2 ml of dimethylformamide. The reaction mixture is chromatographed directly on a chromatography column containing 6 g of silica gel using toluene:ethyl acetate (19:1), to give 60 mg of pure title compound as a non-crystalline solid.

Steps D₁ and D₂:

p-Nitrobenzyl 3-[1,1-dimethyl-2-((1-methyl-1,2,3,4-tetrazol-5-yl)-thio)-ethyl]-7-oxo-4-oxa-1-azabicyclo[3.2.0]hept-2-ene-2-carboxylate

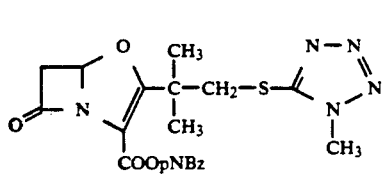

By the process given in Example 1 starting from p-nitrobenzyl 2-(4-tert-butylthio-2-oxo-1-azetidinyl)-4,4-dimethyl-5-[(1-methyl-1,2,3,4-tetrazol-5-yl)-thio]-3-oxopentanoate via steps D₁ and D₂, the title compound was obtained after chromatography over silica gel using toluene: ethyl acetate (3:1) IR spectrum in CH₂CL₂: 2930, 2860, 1810, 1720, 1590, 1525, 1350, 1320, 1175, 1120, 1030, 1015 cm⁻¹.

Step E:

3-[1,1-Dimethyl-2-((1-methyl-1,2,3,4-tetrazol5-yl)-thio)-ethyl]-7-oxo-4-oxa-1-azabicyclo[3.2.0]hept-2-ene-2-carboxylic acid, Na salt

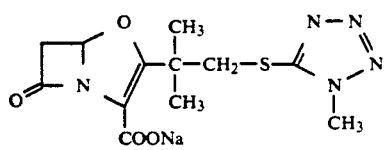

By the process described in Example 1 starting from the appropriate p-nitrobenzyl ester via step E, the title compound was obtained as a white solid (after lyophilization). UV spectrum in H₂O: strong end absorption, shoulder at 270 nm (ε=4000).

EXAMPLE 10

Preparation of 3-[1-Methyl-1-(2-thienyl)-ethyl]-7-oxo-4-oxa-1-azabicyclo[3.2.0]hept-2-ene-2-carboxylic acid, its Na salt and its p-nitrobenzyl ester

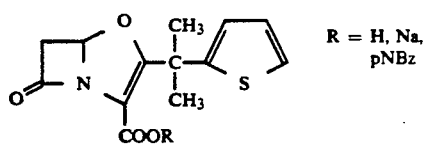

By the process described in Example 1 starting from p-nitrobenzyl 2-(4-tert-butylthio-3,3-dimethyl-2-oxoazetidinyl)acetate and 2-methyl-2-thienylpropionyl chloride via steps C, D₁ and D₂, the title compound (p-nitrobenzyl ester) was obtained as a colourless, non-crystalline solid. IR spectrum in CH₂Cl₂: 2930, 1800, 1720, 1605, 1530, 1350, 1080 cm⁻¹.

Step E:

3-[1-Methyl-1-(2-thienyl)-ethyl]-7-oxo-4-oxa-1azabicyclo[3.2.0]hept-2-ene-2-carboxylic acid, Na salt

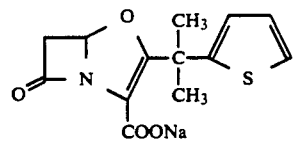

By the process described in Example 1 starting from the appropriate p-nitrobenzyl ester, the pure title compound was obtained as a white solid. UV spectrum in H₂O: $\lambda_{max}$=270 nm (ε=6500)

EXAMPLE 11

Preparation of 2-(2-acetoxy-1,1-dimethylethyl)-7-oxo-4-oxa-1-azabicyclo[3.2.0]hept-2-ene-2-carboxylic acid, its Na salt and its p-nitrobenzyl ester

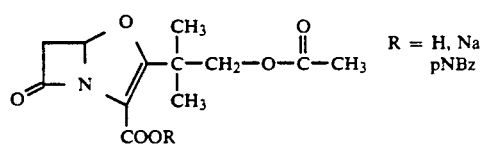

By the process described in Example 1 starting from p-nitrobenzyl 2-(4-tert-butylthio-2-oxoazetidinyl)-acetate and β-acetoxypivaloyl chloride via steps C, D₁ and D₂, the title compound (p-nitrobenzyl ester) was obtained as a slightly yellowish, non-crystalline solid. IR spectrum in CH₂Cl₂: 2950, 2850, 1810, 1740, 1720, 1590, 1550, 1340, 1080 cm⁻¹.

Step E:

2-(2-Acetoxy-1,1-dimethylethyl)-7-oxa-4-oxa1-azabicyclo[3.2.0]hept-2-ene-2-carboxylic acid, Na salt

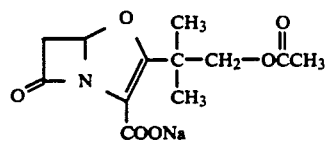

By the process described in Example 1 starting from the appropriate p-nitrobenzyl ester via step E, the title compound was obtained in 70% yield as a non-crystalline, white solid (lyophilisate). UV spectrum in H₂O: $\lambda_{max}$=270 nm (ε=6300). NMR spectrum in D₂O: δ=1.25 (s, 3 H), 1.26 (s, 3 H) 2.06 (s, 3 H), 3.40 (dd, J=1 Hz, J=17 Hz, 2 H), 3.72 (dd, J=3 Hz, J=17 Hz, 2 H), 4.23 (AB, J=17 Hz, 2 H), 5.80 (dd, J=1 Hz, J=3 Hz, 1 H).

EXAMPLE 12

Preparation of 3-tert-butyl-6-(1-hydroxyethyl)-7-oxo-4-oxa-1-azabicylo[3.2.0]hept-2-ene-2-carboxylic acid, its Na salt and its p-nitrobenzyl ester

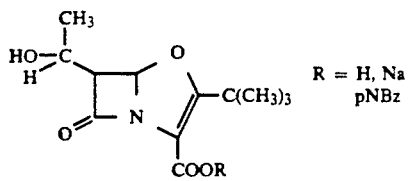

R = H, Na
pNBz

Step A₂:

4-Methylthio-3-[1-(p-nitrobenzyloxycarbonyloxy)-ethyl]-azetidin-2-one

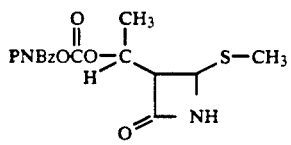

1.17 g (16.7 mmol) of the Na salt of methyl mercaptan are added to a solution of 4.48 g (11.1 mmol) of 4-(2-hydroxyethylsulphonyl)-3-[1-(p-nitrobenzyloxycarbonyloxy)-ethyl]-azetidin-2-one in 11 ml of acetonitrile and 11 ml of H₂O at 0° C., and the mixture is stirred at 0° C. for 20 minutes. The reaction mixture is diluted with 100 ml of methylene chloride and 25 ml of H₂O, and, after separating off the organic phase, the aqueous phase is extracted three times with 25 ml of methylene chloride in each case. The combined organic phases are dried over MgSO₄, filtered and the solvent is removed in vacuo, to give 3.80 g of the title compound as a slightly yellowish non-crystalline compound. NMR spectrum in CDCl₃: δ=1.45 (d, J=7 Hz, 3 H), 2.12 (s, 3 H), 3.3 (dd, J=7 Hz, J=2 Hz), 4.70 (d, J=2 Hz, 1 H), 5.12 (m, 1 H), 5.20 (s, 2 H), 6.45 (broad s, 1 H), 7.50 (d, J=8.5 Hz, 2 H), 8.20 (d, J=8.5 Hz, 2 H).

Step B:

p-Nitrobenzyl 2-[4-methylthio-3-(1-(p-nitrobenzyloxycarbonyloxy)-ethyl)-2-oxoazetidinyl]acetate

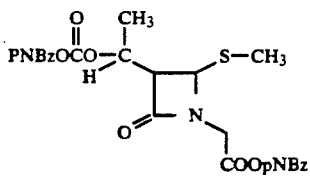

2.2 ml of 1M solution of lithium bis(trimethylsilylamide) are added over the course of 5 minutes to a stirred mixture, at 70° C., of 680 mg (2 mmol) of 4-methylthio-3-[1-(p-nitrobenzyloxycarbonyloxy)-ethyl]-azetidin-2-one and 602 mg (2.2 mmol) of p-nitrobenzyl bromoacetate in 2 ml of dry tetrahydrofuran and 2 ml of dry DMF. The reaction mixture is stirred at −70° C. for 30 minutes, diluted with 30 ml of ethyl acetate and 70 ml of toluene and washed twice with dilute NaCl solution. The organic phase is dried over MgSO₄ and filtered, and the solvent is evaporated in vacuo. The residue is chromatographed over 65 g of silica gel using toluene:ethyl acetate 4:1, to give 520 mg of a yellow oil. IR spectrum in CH₂Cl₂: 2920, 2850, 1765, 1750, 1605, 1520, 1355, 1345 cm⁻¹.

Step C:

p-Nitrobenzyl 4,4-dimethyl-2-[4-methylthio-3-(1-(p-nitrobenzyloxycarbonyloxy)-ethyl)-2-oxoazetidinyl]-3-oxopentanoate

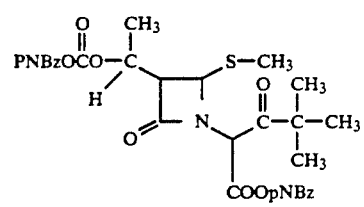

1.1 ml of 1M lithium bis(trimethylsilyl)amide are added over the course of 5 minutes to a stirred mixture of 275 mg (0.515 mmol) of p-nitrobenzyl 2-[4-methylthio-3-(1-(p-nitrobenzyloxycarbonyloxy)-ethyl)-2-oxoazetidinyl]-acetate and 67 μl (0.55 mmol) of pivaloyl chloride in 6.7 ml of dry tetrahydrofuran at −70° C., and the reaction mixture is stirred at −70° C. for a further 30 minutes and then diluted with 40 ml of toluene and washed with 30 ml of 2N HCl, then twice with 40 ml of NaCl solution in each case. The organic phase is dried over MgSO₄ and filtered, and the solvent is removed in vacuo. The residue is chromatographed over 10 g of silica gel using toluene:ethyl acetate (9:1), to give 268 g of a white, non-crystalline solid. IR spectrum in CH₂Cl₂: 2930, 2850, 1775, 1760, 1720, 1610, 1535, 1350 cm⁻¹.

Step D₁:

p-Nitrobenzyl 2-[4-chloro-3-(1-(p-nitrobenzyloxycarbonyloxy)-ethyl)-2-oxoazetidinyl]-4,4-dimethyl-3-oxopentanoate

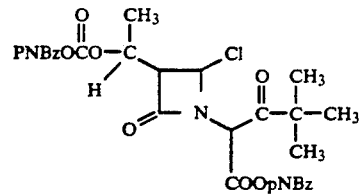

660 μl of a solution containing 850 mg of chlorine in 10 ml of carbon tetrachloride is added to a solution of 244 mg (0.395 mmol) of p-nitrobenzyl 4,4-dimethyl-2-[4-methylthio-3-(1-(p-nitrobenzyloxycarbonyloxy)-ethyl)-2-oxoazetidinyl]-3-oxopentanoate in 16 ml of methylene chloride at −60° C. The pale yellow solution is stirred at −60° C. for 2 hours, and the solvent is removed in vacuo, to give 236 mg of a colourless, non-crystalline solid. IR spectrum in CH₂Cl₂: 2930, 2850, 1795, 1765, 1725, 1620, 1530, 1355 cm⁻¹.

Step D₂:

p-Nitrobenzyl
3-tert-butyl-6-[1-(p-nitrobenzyloxycarbonyloxy)ethyl]-7-oxo-4-oxa-1-azabicyclo[3.2.0]hept-2-carboxylate

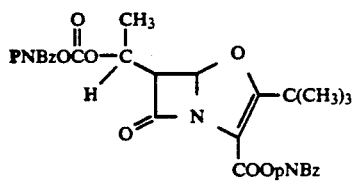

476 μl of 0.75M potassium tert-butoxide in tert-butanol are added to a stirred solution of 214 mg of p-nitrobenzyl 2-[4-chloro-3-(1-(p-nitrobenzyloxycarbonyloxy)-ethyl)-2-oxoazetidinyl]-4,4-dimethyl-3-oxopentanoate in 7 ml of dry tetrahydrofuran at −30° C., and the reaction mixture is subsequently stirred at −30° C. for 30 minutes. The reaction solution is diluted with 40 ml of ethyl acetate and subsequently washed with 40 of dilute NaCl solution and with 40 ml of saturated NaCl solution. The organic phase is dried over MgSO₄ and filtered, and the solvent is evaporated in vacuo to give 198 mg of a residue, which is chromatographed over 6 g of silica gel using toluene/ethyl acetate to give 183 mg of a colourless, non-crystalline solid (title compound). IR spectrum in CH₂Cl₂; 3030, 2950, 1805, 1755, 1720, 1610, 1580, 1530, 1350, 1320, 1090 cm⁻¹.

Step E:

Simultaneous removal of two protecting groups, 3-tert-butyl-6-(1-hydroxyethyl)-7-oxo-4-oxa-1-azabicyclo[3.2.0]hept-2-ene-2-carboxylic acid, Na salt

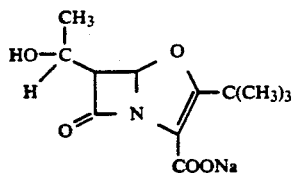

A solution of 28 mg (0.05 mmol) of p-nitrobenzyl 3-tert-butyl-6-[1-(p-nitrobenzylcarbonyloxy)-ethyl]-7-oxo-4-oxa-1-azabicyclo[3.2.0]hept-2-ene-2-carboxylate in 1 ml of ethyl acetate is injected through a septum stopper into a pre-hydrogenated mixture, at 0° C., of 84 mg of Pd/C (10%), 4.6 mg of NaHCO₃ in 1 ml of ethyl acetate and 0.7 ml of H₂O, and the mixture is hydrogenated for 40 minutes at 0° C., during which 8.0 ml of H₂ are taken up (theoretical value about 8.8 ml of H₂). The mixture is filtered at 0° C., and the aqueous phase is washed a further twice with 2 ml of pre-cooled ethyl acetate in each case and then lyophilized in a high vacuum, to give 11 mg of a white, non-crystalline solid (title compound). UV spectrum in H₂O: $\lambda_{max}$=278 nm ($\epsilon$=5500).

EXAMPLE 13

Preparation of
3-tert-butyl-6-hydroxymethyl-7-oxo-4-oxa-1-azabicyclo[3.2.0]hept-2-ene-2-carboxylic acid and its Na salt

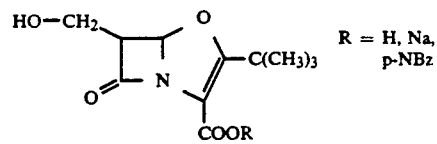

By the process described in Example 12 starting from 4-(2-hydroxyethylsulphonyl)-3-(p-nitrobenzyloxycarbonyloxymethyl)-azetidin-2-one via steps A₂, B, C, D₁, D₂ and E, the title compound (Na salt) was obtained as a white, non-crystalline solid (lyophilized). UV spectrum in H₂O: $\lambda_{max}$=275 nm ($\epsilon$=5500). The potassium salt of 3-tert-butyl-6-hydroxymethyl-7-oxo-4-oxa-1-azabicyclo[3.2.0]hept-2-ene-2-carboxylic acid was prepared in analogously.

EXAMPLE 14

Preparation of
2-tert-butyl-6-ethylidene-1-oxapen-2-em-3-carboxylic acid, its Na salt and its p-nitrobenzyl ester

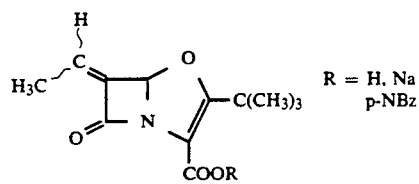

Starting from 4-tert-butylthio-3-ethylideneazetidin-2-one and using the reagents and reaction conditions mentioned in Example 12, via steps B, C, D and D₂, the title compound (p-nitrobenzyl ester) is obtained (p-nitrobenzyl 3-tert-butyl-6-ethylidene-4-oxa-7-oxo-1-azabicyclo[3.2.0]hept-2-ene-2-carboxylate). IR spectrum in CH₂Cl₂: 1800, 1720, 1585, 1525, 1345, 1310, 1165 cm⁻¹.

Step E:

3-tert-Butyl-6-ethylidene-4-oxa-7-oxo-1-azabicyclo[3.2.0]hept-2-ene-2-carboxylic acid, Na salt

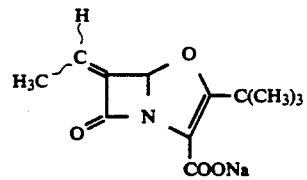

Starting from the appropriate p-nitrobenzyl ester, using the reaction conditions mentioned in Example 12 and using Pd on PbCO₃ instead of Pd on C as catalyst, the title compound was obtained after a reaction time of 4 hours (white lyophilisate). UV spectrum in H₂O: $\lambda_{max}$=272 ($\epsilon$=5100).

EXAMPLE 15

Preparation of pharmaceutical preparations

A unit dose form is prepared by mixing 120 mg of 3-tert-butyl-6-(1-hydroxyethyl)-7-oxo-4-oxa-1-azabicyclo[3.2.0]hept-2-ene-2-carboxylic acid, Na salt, with 20 mg of lactose and 5 mg of magnesium stearate and transferring the 145 mg mixture into a No. 3 gelatin capsule. Similarly, if more active component and less lactose are used, other dose forms can be prepared and transferred into No. 3 gelatin capsules; and, should it be necessary to mix more than 145 mg of components together, larger capsules, such as, in addition, compressed tablets and pills, can likewise be produced. The examples below illustrate the preparation of pharmaceutical preparations.

| Tablet | Tablet, mg |
| --- | --- |
| 3-tert-butyl-6-(1-hydroxyethyl)-7-oxo-4-1hept-2-ene-2-carboxylic acid, Na salt | 125 |
| Maize starch, U.S.P. | 6 |
| Dicalcium phosphate | 192 |
| Lactose, U.S.P. | 190 |

The active component is mixed with the dicalcium phosphate, lactose and about half of the maize starch, The mixture is then granulated together with 6 mg of 15% strength maize starch paste and coarsely sieved. It is dried at 45° C. and re-sieved through sieves of mesh width 1.00 mm (No. 16 screens). The remainder of the maize starch and the magnesium stearate are added, and the mixture is compressed to form tablets each weighing 800 mg and having a diameter of 1.27 cm (0.5 in.).

Parenteral solution

| Ampules | |
| --- | --- |
| 3-tert-butyl-6-(1-hydroxyethyl)-7-oxo-4-oxa-1-azabicyclo[3.2.0]hept-2-ene-2-carboxylic acid, Na salt | 500 mg |
| sterile water | 2 ml |
| Ophthalmic solution | |
| 3-tert-butyl-6-(1-hydroxyethyl)-7-oxo-4-oxa-1-azabicyclo[3.2.0]hept-2-ene-2-carboxylic acid, Na salt | 100 mg |
| hydroxypropylmethylcellulose | 5 mg |
| sterile water to | 1 ml |
| Otic solution | |
| 3-tert-butyl-6-(1-hydroxyethyl)-7-oxo-4-oxa-1-azabicyclo[3.2.0]hept-2-ene-2-carboxylic acid, Na salt | 100 mg |
| benzalkonium chloride | 0.1 mg |
| sterile water to | 1 ml |
| Topical cream or ointment | |
| 3-tert-butyl-6-(1-hydroxyethyl)-7-oxo-4-oxa-1-azabicyclo[3.2.0]hept-2-ene-2-carboxylic acid, Na salt | 100 mg |
| polyethylene glycol 4000 U.S.P. | 400 mg |
| polyethylene glycol 400 U.S.A.P. | 1.0 g |

The active component in the above preparations can be mixed alone or together with other biologically active components, for example with other antibacterial agents, such as lincomycin, a penicillin, streptomycin, novobiocin, gentamicin, neomycin, colistin and kanamycin, or with other therapeutic agents, such as probenecid.

We claim:

1. A compound of the structural formula

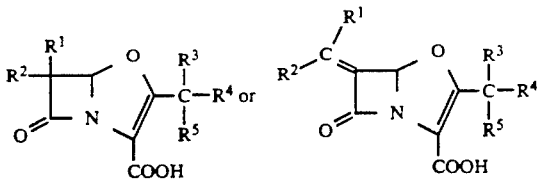

in which $R^1$ and $R^2$, independently of one another, denote hydrogen or pharmaceutically acceptable groups which are bonded to the remaining part of the molecule via carbon-carbon single bonds and are selected from the group consisting of substituted or unsubstituted alkyl, alkenyl, alkinyl, cycloalkyl, alkylcycloalkyl, alkylcycloalkenyl, cycloalkylalkyl, alkenylcycloalkyl, cycloalkenylalkyl, aryl, aralkyl, aralkenyl, aralkinyl, carboxyl or cyano, where the foregoing alkyl, alkenyl or alkinyl molecule parts contain 1 to 6 carbon atoms, and the cycloalkyl or cycloalkenyl molecule parts contain 3 to 6 carbon atoms and the aryl molecule parts contain 6 to 10 carbon atoms, heterocyclyl, heterocyclylalkyl, heterocyclylalkenyl, heterocyclylalkinyl or alkylheterocyclyl, where the foregoing alkyl, alkenyl or alkinyl molecule parts contain 1 to 6 carbon atoms and the heterocyclic molecule part is monocyclic or bicyclic and contains 3 to 10 ring atoms, of which one or more are selected from the group consisting of oxygen, sulphur and nitrogen, and where the substituents of the abovementioned groups may be protected or unprotected hydroxyl, hydroxyalkoxy, aminoalkoxy, amidinoalkoxy, alkoxy, acyloxy, aryloxy, heterocyclyloxy, carbamoyl, carbamoyloxy, thiocarbamoyl, thiocarbamoyloxy, alkylcarbamoyloxy, alkylthiocarbamoyloxy, mercapto, alkylthio, hydroxyalkylthio, aminoalkylthio, amidinoalkylthio, acylthio, arylthio, alkylheterocyclylthio, hydroxyalkylheterocyclylthio, heterocyclylthio, carbamoylthio, alkylcarbamoylthio, thiocarbamoylthio or alkylthiocarbamoylthio, protected or unprotected amino or monoalkylamino, dialkylamino, oxo, protected or unprotected oximino or alkylamino, cycloalkylamino, arylamino, heterocyclylamino, alkanoylamino, amidino, alkylamidino, guanidino, alkylguanidino, carbamoylamino, alkylcarbamoylamino, thiocarbamoylamino, alkylthiocarbamoylamino, nitro, chlorine, bromine, fluorine, iodine, azido, cyano, alkylsulphinyl, alkylsulphonyl, sulphonamido, sulphamoyloxy, alkylsulphonyloxy or protected or unprotected sulpho, sulphoxy or carboxyl, where the substituents, independently of one another, occur once or several times and their alkyl molecule part contains 1 to 6 carbon atoms and their aryl molecule part contains 6 to 10 carbon atoms, and where the heterocylic molecule part is monocyclic or bicyclic and contains 3 to 10 ring atoms, of which one or more are selected from the group consisting of oxygen, sulphur and nitrogen, and $R^3$, $R^4$ and $R^5$, independently of one another, are selected from the abovementioned, pharmaceutically acceptable groups which are bonded to the remaining part of the molecule via carbon-carbon single bonds.

2. A compound according to claim 1, in which $R^1$ and $R^2$, independently of one another, denote hydrogen, alkyl, protected or unprotected hydroxyalkyl or protected or unprotected dihydroxyalkyl, each having 1 to 6 carbon atoms.

3. A compound according to claim 1, in which $R^3$ and $R^4$ denote methyl, and $R^5$ is selected from the group consisting of $CH_3$,

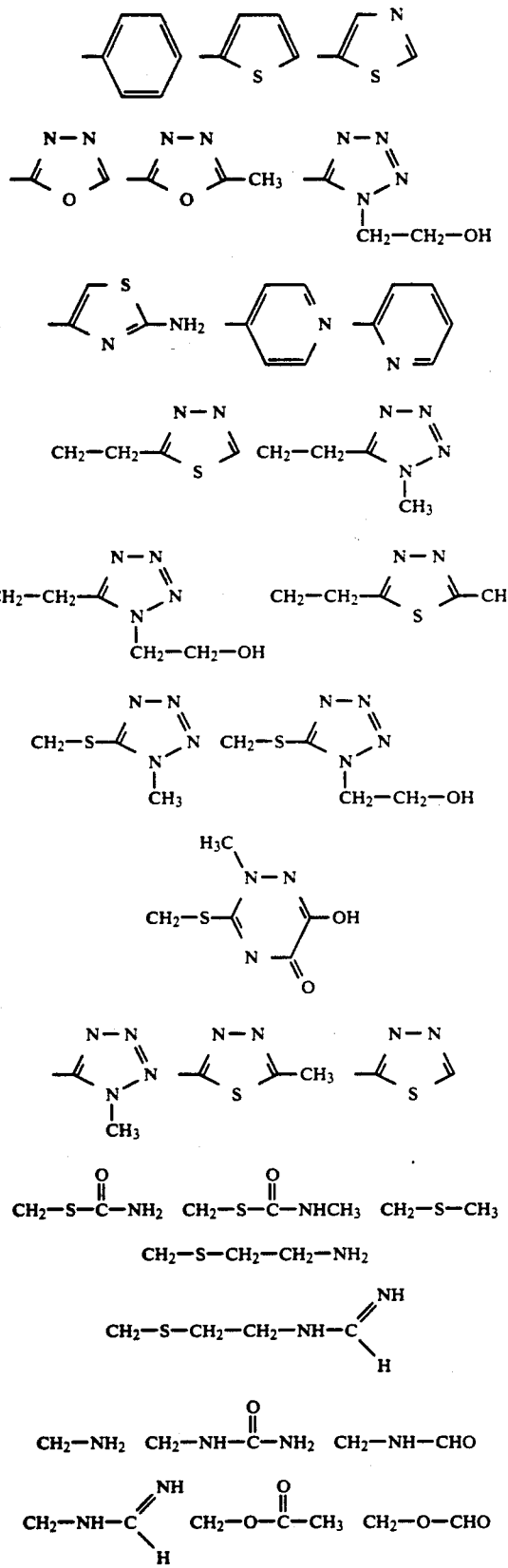

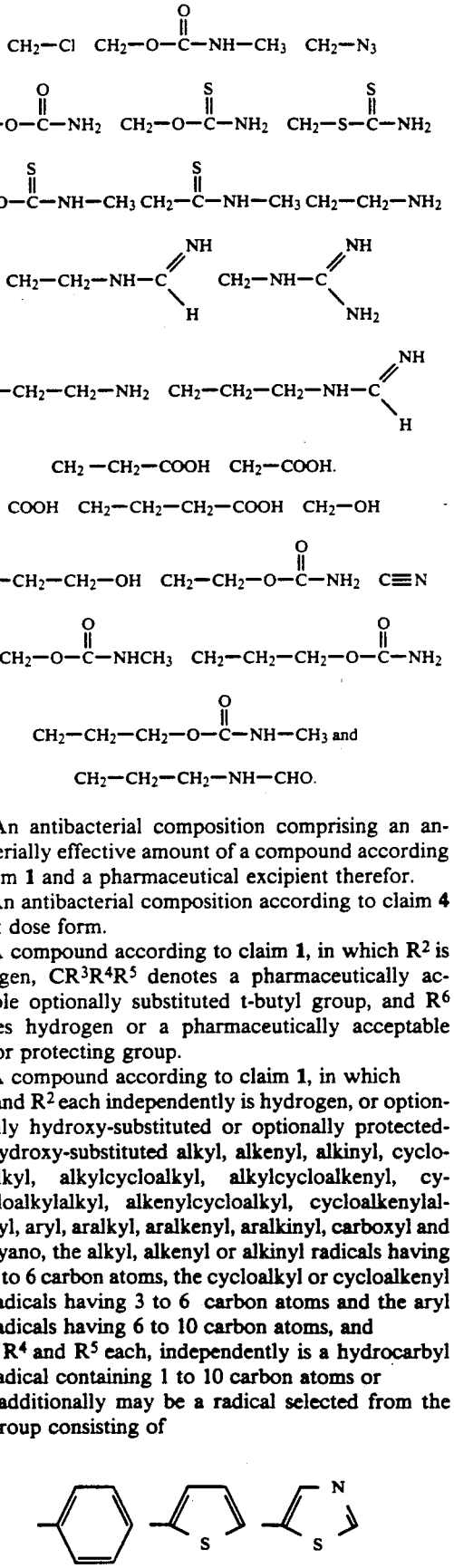

4. An antibacterial composition comprising an antibacterially effective amount of a compound according to claim 1 and a pharmaceutical excipient therefor.

5. An antibacterial composition according to claim 4 in unit dose form.

6. A compound according to claim 1, in which $R^2$ is hydrogen, $CR^3R^4R^5$ denotes a pharmaceutically acceptable optionally substituted t-butyl group, and $R^6$ denotes hydrogen or a pharmaceutically acceptable ester or protecting group.

7. A compound according to claim 1, in which
$R^1$ and $R^2$ each independently is hydrogen, or optionally hydroxy-substituted or optionally protected-hydroxy-substituted alkyl, alkenyl, alkinyl, cycloalkyl, alkylcycloalkyl, alkylcycloalkenyl, cycloalkylalkyl, alkenylcycloalkyl, cycloalkenylalkyl, aryl, aralkyl, aralkenyl, aralkinyl, carboxyl and cyano, the alkyl, alkenyl or alkinyl radicals having 1 to 6 carbon atoms, the cycloalkyl or cycloalkenyl radicals having 3 to 6 carbon atoms and the aryl radicals having 6 to 10 carbon atoms, and
$R^3$, $R^4$ and $R^5$ each, independently is a hydrocarbyl radical containing 1 to 10 carbon atoms or
$R^5$ additionally may be a radical selected from the group consisting of -continued

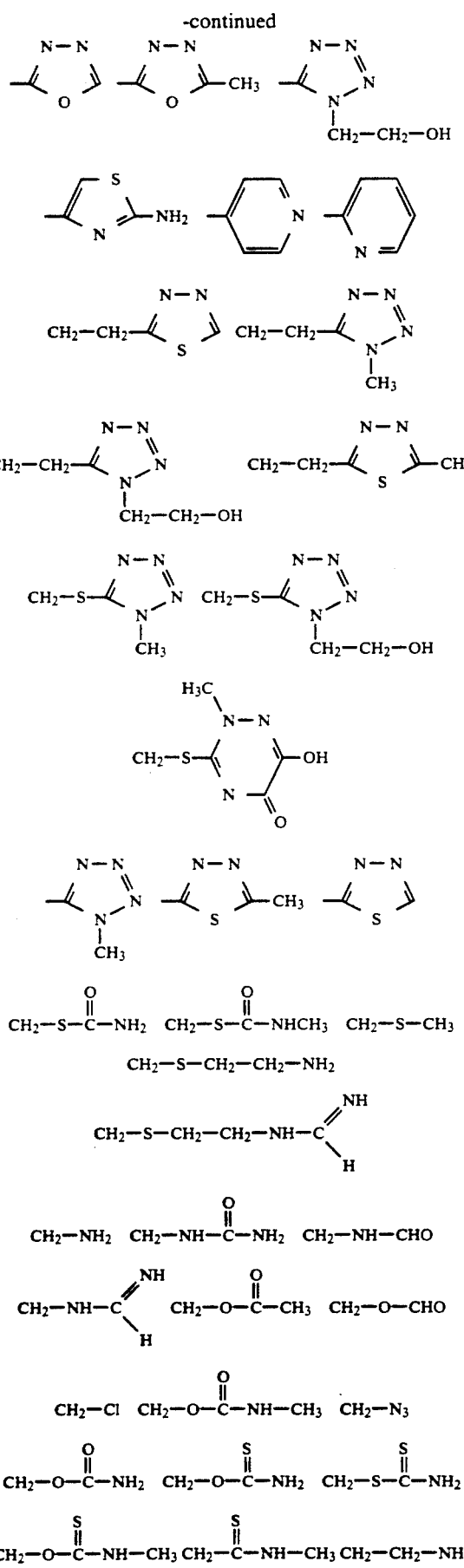

-continued

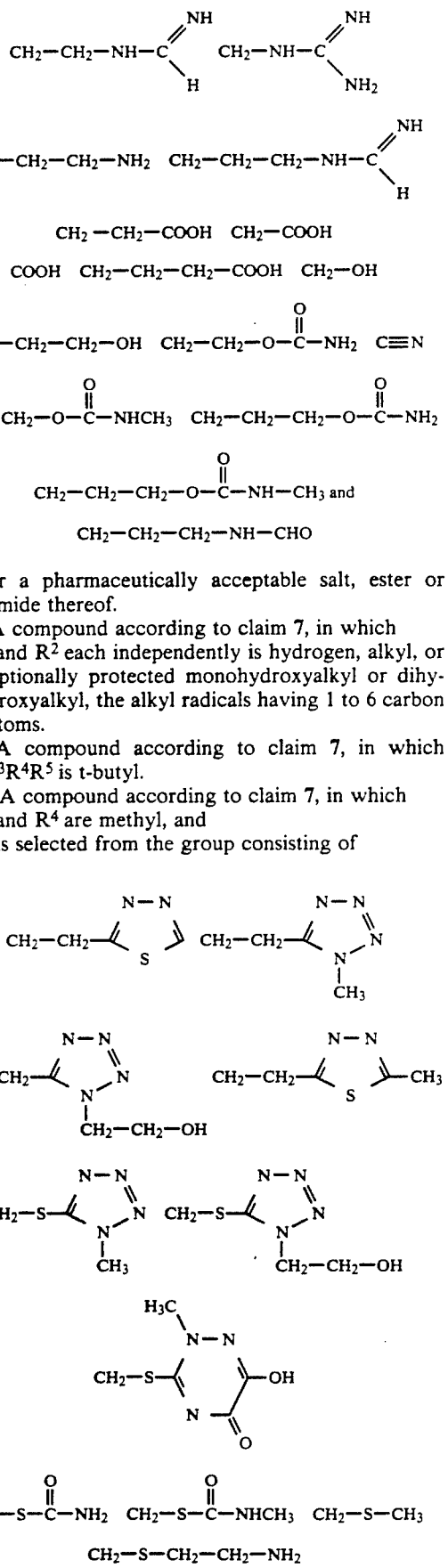

or a pharmaceutically acceptable salt, ester or amide thereof.

8. A compound according to claim 7, in which $R^1$ and $R^2$ each independently is hydrogen, alkyl, or optionally protected monohydroxyalkyl or dihydroxyalkyl, the alkyl radicals having 1 to 6 carbon atoms.

9. A compound according to claim 7, in which $-CR^3R^4R^5$ is t-butyl.

10. A compound according to claim 7, in which $R^3$ and $R^4$ are methyl, and $R^5$ is selected from the group consisting of -continued

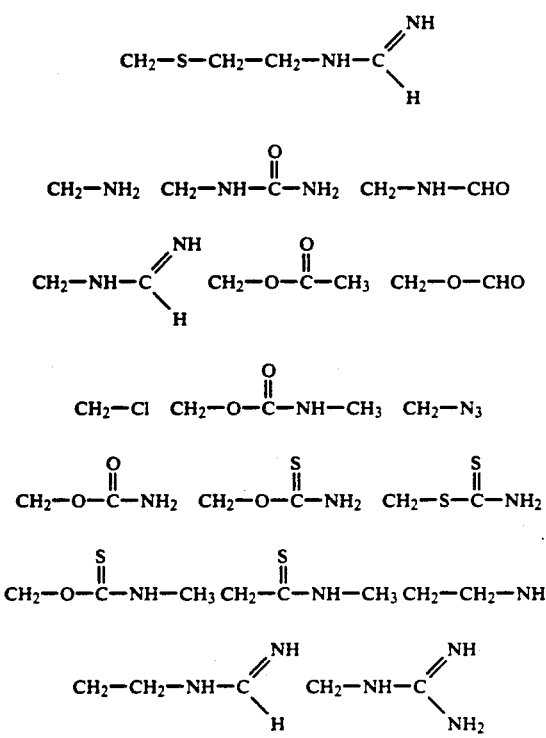

-continued

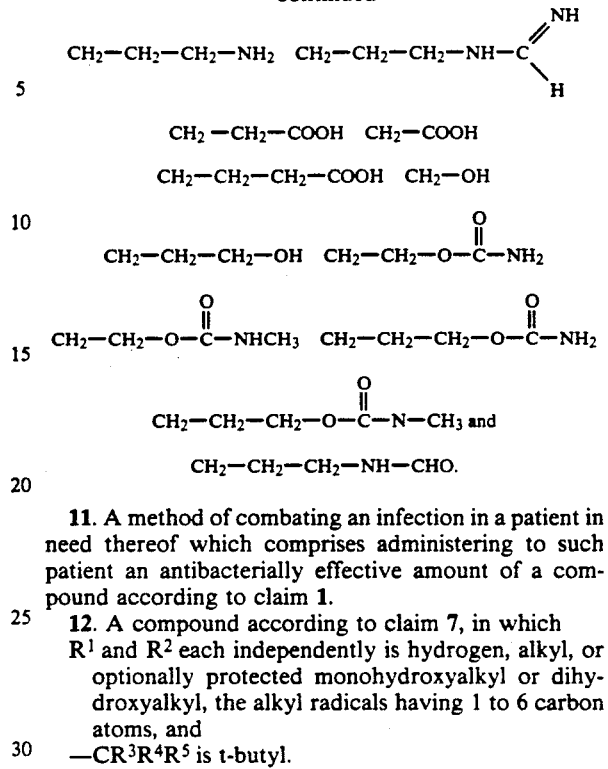

11. A method of combating an infection in a patient in need thereof which comprises administering to such patient an antibacterially effective amount of a compound according to claim 1.

12. A compound according to claim 7, in which
R$^1$ and R$^2$ each independently is hydrogen, alkyl, or optionally protected monohydroxyalkyl or dihydroxyalkyl, the alkyl radicals having 1 to 6 carbon atoms, and
—CR$^3$R$^4$R$^5$ is t-butyl.

* * * * *

UNITED STATES PATENT AND TRADEMARK OFFICE
CERTIFICATE OF CORRECTION

PATENT NO. : 5,096,899

DATED : March 17, 1992

INVENTOR(S) : Pfaendler et al.

It is certified that error appears in the above-identified patent and that said Letters Patent is hereby corrected as shown below:

Title Page      ABSTRACT: Last two lines delete " axapenemcarboxylic " and substitute -- oxapenemcarboxylic --

Col. 46, line 18    Delete " $CH_2-CH_2-CH_2-O-\overset{\overset{O}{\|}}{C}-N-CH_3$ " and substitute -- $CH_2-CH_2-CH_2-O-\overset{\overset{O}{\|}}{C}-NH-CH_3$ --

Signed and Sealed this

Twentieth Day of July, 1993

Attest:

MICHAEL K. KIRK

*Attesting Officer*      *Acting Commissioner of Patents and Trademarks*